US011559575B2

(12) United States Patent
Bras Gonçalves et al.

(10) Patent No.: US 11,559,575 B2
(45) Date of Patent: Jan. 24, 2023

(54) MULTI-EPITOPIC PEPTIDE COMPOUNDS AND VACCINES AGAINST LEISHMANIASIS

(71) Applicants: INSTITUT DE RECHERCHE POUR LE DEVELOPPEMENT, Marseilles (FR); INSTITUT PASTEUR DE TUNIS, Tunis (TN)

(72) Inventors: Rachel Bras Gonçalves, Montpellier (FR); Jean-Loup Lemesre, Montpellier (FR); Amel Garnaoui, Tunis (TN); Elodie Petitdidier-Lesin, Prades-le-Lez (FR)

(73) Assignees: INSTITUT DE RECHERCHE POUR LE DEVELOPPEMENT, Marseilles (FR); INSTITUT PASTEUR DE TUNIS, Tunis (TN)

( * ) Notice: Subject to any disclaimer, the term of this patent is extended or adjusted under 35 U.S.C. 154(b) by 0 days.

(21) Appl. No.: 17/059,399

(22) PCT Filed: May 29, 2019

(86) PCT No.: PCT/EP2019/064088
§ 371 (c)(1),
(2) Date: Nov. 27, 2020

(87) PCT Pub. No.: WO2019/243018
PCT Pub. Date: Dec. 26, 2019

(65) Prior Publication Data
US 2021/0213114 A1    Jul. 15, 2021

(30) Foreign Application Priority Data
May 30, 2018  (FR) ...................... 1800533

(51) Int. Cl.
*A61K 39/008* (2006.01)
*A61K 39/00* (2006.01)

(52) U.S. Cl.
CPC .. *A61K 39/008* (2013.01); *A61K 2039/55505* (2013.01); *A61K 2039/55516* (2013.01); *A61K 2039/55522* (2013.01); *A61K 2039/55555* (2013.01); *A61K 2039/55577* (2013.01); *A61K 2039/55583* (2013.01)

(58) Field of Classification Search
None
See application file for complete search history.

(56) References Cited

U.S. PATENT DOCUMENTS

| | | |
|---|---|---|
| 9,804,158 B2 | 10/2017 | Arevalo et al. |
| 2016/0146809 A1 | 5/2016 | Arevalo et al. |
| 2016/0186158 A1 | 6/2016 | Duthie et al. |

FOREIGN PATENT DOCUMENTS

| | | |
|---|---|---|
| WO | 2014102471 A1 | 7/2014 |
| WO | 2014160987 A2 | 10/2014 |
| WO | 2015001383 A1 | 1/2015 |

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council, pp. 5-7).*
International Search Report and Written Opinion dated Oct. 17, 2019 in corresponding application No. PCT/EP2019/064088; with English partial translation and partial machine translation (total 32 pages).
Martins et al., "A recombinant fusion protein displaying murine and human MHC class I- and II-specific epitopes protects against Leishmania amazonensis infection" Cellular Immunology, Academic Press, San Diego, CA (US), vol. 313, 2017 (Dec. 28, 2016), pp. 32-42 (in English).
Vijayamahantesh et al., "Immuno-informatics based approaches to identify CD8+ T cell epitopes within the Leishmania donovani3-ectonucleotidase in cured visceral leishmaniasis subjects", Microbes and Infection, Elsevier, Paris (FR), vol. 19, No. 6, 2017 (Apr. 1, 2017), pp. 358-369 (in English).
Kashyap et al., "Prediction and analysis of promiscuous T cell-epitopes derived from the vaccine candidate antigens of Leishmania donovani binding to MHC class-II alleles using in silicoapproach", Infection, Genetics and Evolution, Elsevier, Amsterdam (NL), vol. 53, 2017 (May 23, 2017), pp. 107-115 (in English).
Dikhit et al., "Mining the Proteome of Leishmania donovani for the Development of Novel MHC Class I Restricted Epitope for the Control of Visceral Leishmaniasis", Journal of Cellular Biochemistry, vol. 119, No. 1, 2018 (Jan. 2018), pp. 378-391 (in English).
Elfaki et al., "Immunogenicity and immune modulatory effects of in silico predicted L. donovani candidate peptide vaccines". Human Vaccines & Immunotherapeutics, vol. 8, No. 12, 2012 (Dec. 2012), pp. 1769-1774 (in English).

* cited by examiner

*Primary Examiner* — Jennifer E Graser
(74) *Attorney, Agent, or Firm* — Seckel IP, PLLC

(57) ABSTRACT

The invention relates to multi-epitopic peptide compounds obtained from PSA, HwB and LmLRAB proteins of *Leishmania* as well as to pharmaceutical compositions and vaccines for use against one or more leishmaniases.

22 Claims, 7 Drawing Sheets

Specification includes a Sequence Listing.

FIG. 1

```
RABLmaj     1    MSSTSQRVNIGDAEDYTYTEDPAGQRVEVPVSKEYVFKVVILGDYSVGKT
RABLmaj    51    SLIKRLLSIPASGASPRSHEDCSDMDDSVGDSDADEALATVTPTVGTDFY
RABLmaj   101    SLALPDVIPGASVRLQIWDTAGLEKYAASYKSTIRNASFVICVFDVTNPS RABLmaj   151    SLRSVVGRHLSIVADHVPHLDQSSIMVVANKIDIIVDVSTNSEALRSARS
SEQ_ID_74        ---------------MPHVDQSSI-------------------------
SEQ_ID_76        ----------------SSIMVVANK------------------------

RABLmaj   201    RARLPENAFVIAVEKEASMDTSDSSPDIFTSAKGASKNAIVTSRKVQERV
SEQ_ID_71        --RLPENAFVI--------------------------------------

RABLmaj   251    FDLFTDVHYSEVSAKTEQHLREMLHAVCYALLRNSVGDNPNIQIPDSTPP
SEQ_ID_68        -----------KTEQHLREM-----------------------------

RABLmaj   301    SEVFAHTVLPPHSGAKCPTGASAGTFSAPQLDPAATKTFEAAVPRDSPTR

RABLmaj   351    GSLQPPERTTPAFPAASWRSTEAISFDLSPTQFSSKAGFSPAEGSDGAIG
SEQ_ID_72        -------------------TQGSSKAGF---------------------
SEQ_ID_75        ---------ASFRSTEAI-------------------------------

RABLmaj   401    KSGGEDSAPQRVGSGGDSPVDGSETRLPTPRGNLAKAVDASGVRLDLIAG
RABLmaj   451    STRQSTGPNRREDPKARKEREQTEMKAVLSCAGQRKVNPNGGGTDTQRSA RABLmaj   501    AWLQNDADRMENNITLGLKKAGDAPSAARPAPVSSILDSHGVQGRCKGNQ
SEQ_ID_67        ----------MENNITGGL------------------------------

RABLmaj   551    GTRGRDSDDDDGARMQLQLKHRFAQIEHDIRQNAAAANQRAKHAKKSTK
SEQ_ID_70        -----------------RFAQGEHDI-----------------------

RABLmaj   601    AKSFCNCCVL
```

FIG. 2A

```
RABLmaj   1   MSSTGQHVNIGDADDYTYTEDPAGQRVKVPVSKEYVFKVVILGDYSVGKTSLIKRLLSIP
RABLmaj  61   ASGASPRSHEICSIMDDSVGDSDADDALATVTPTVGTDFYSLALPDVIPGASVRLQIWDT RABLmaj 121   AGLEKYAASYESTLRNASFVICVFDVTNPSSLHSVVGRHLSIVADHVPHLDQSSIMVVAN
SEQ_ID_78    ------------------------------KGRLHSVVGRHLSIV---------------
SEQ_ID_79    -------------------------------GRLHSVVGRHLSIVA--------------
SEQ_ID_80    --------------------------------RLHSVVGRHLSIVAD-------------
SEQ_ID_81    ---------------------------------LHSVVGRHLSIVADH------------
SEQ_ID_82    ----------------------------------HSVVGRHLSIVADHM-----------
SEQ_ID_83    -----------------------------------SVVGRHLSIVADHMP----------
SEQ_ID_84    ------------------------------------VVGRHLSIVADHMPH---------
SEQ_ID_85    -------------------------------------VGRHLSIVADHMPHL--------
SEQ_ID_86    --------------------------------------GRHLSIVADHMPHLD-------
SEQ_ID_87    ---------------------------------------RHLSIVADHMPHLDQ------
SEQ_ID_88    ----------------------------------HLSIVADHM----------------
SEQ_ID_89    -------------------------------------IVADHMPHL-------------
SEQ_ID_90    ---------------------------LHSVVGRHL-----------------------
SEQ_ID_91    -----------------------------VGRHLSIVA---------------------
SEQ_ID_92    ------------------------KGRLHSVVG--------------------------
SEQ_ID_93    --------------------------RLHSVVGRH------------------------
SEQ_ID_94    -----------------------------SVVGRHLSI--------------------
SEQ_ID_95    ------------------------------VVGRHLSIV-------------------
SEQ_ID_96    --------------------------LHSVVGRHLSIVADHMPHLDQ------------
SEQ_ID_97    ------------------------KGRLHSVVGRHLSIVADHMPHLDQ-----------

RABLmaj 181   KIDLIVDVSTNSEALRSARKRARLPENAFVIAVDEEASMDTSDSSPDIFTSAEGASENAI
RABLmaj 241   VTSRKVQEEVFDLFTDVHYSEVSAKTKQHLREMLHAVCYALLPNSVGDNPNIQIPDGTPP
RABLmaj 301   SEVFAHTVLPPHSGAKCPTGASAGTFSAPQLDPAATKTPPAAVPRDSPTRGSLQPPPRTT
RABLmaj 361   PAPPAASWRSTEAISFDLSPTQFSSKAGFSPAEGSDGAIGKSGGDDSAPQRVGSGGDSPV
RABLmaj 421   DGSSTRLPTPRGNLAKAVDAGGVHLDLTAGSTEQGTGPNRKEDPKARKEREQTEMKAVLS
RABLmaj 481   CAGQRKVNPNGGGTDTGRSAAWLQNDADRMENNITLGLKKAGDAPSAARPAPVSSILDSH
RABLmaj 541   GVQGRCKGNQGTRGRDSDDDDDGARMQLQLKRRFAQIEHDIRQNAAAANQRAKRAKKRTK
RABLmaj 601   AKGKCNCCVL
```

FIG. 2B

```
RABLmaj   1  MSSTGQRVNIGDADDYTYTEDPAGQRVRVPVSKEYVFKVVILGDYSVGKTSLIKRLLSIPASGASPRSHE
RABLmaj  71  DCSDMDDSVGDSDASDALATVTPTVGTDFYSLALPDVIPGASVRLQIWDTAGLEKYAASYESTLRNASFV
RABLmaj 141  ICVFDVTNPSSLRSVVGRHLSIVADRVPHLDQSSIMVVANKIDIIVDVSTNSEALRSAPKRARLPENAIV RABLmaj 211  IAVDKEASMDTSDSSPDIFTSAEGASKNAIVTSRKVQEEVFDLFTDVHYSEVSAKTKQHLREMLRAVCYA
SEQ_ID_98   ------------------------AIVTSRKVQEEVFDL------------------------------
SEQ_ID_99   ----------------------------------DLFTDVHYSEVSAKT-------------------
SEQ_ID_100  -----------------------------EEVFDLFTDVHYSEV------------------------
SEQ_ID_101  --------------------KNAIVTSRKVQEEVF----------------------------------
SEQ_ID_102  -------------------------------EVFDLFTDVHYSEVS----------------------
SEQ_ID_103  ---------------------------------FDLFTDVHYSEVSAK--------------------
SEQ_ID_104  -------------------GRSENAIVTSRKVQE-----------------------------------
SEQ_ID_105  -------------------------IVTSRKVQEEVFDLF----------------------------
SEQ_ID_106  ------------------KGRSENAIVTSRKVQ------------------------------------
SEQ_ID_107  ----------------------------KVQEEVFDLFTDVHY-------------------------
SEQ_ID_108  ---------------------------------LFTDVHYSEVSAKTK--------------------
SEQ_ID_109  -------------------------NAIVTSRKVQEEVFD----------------------------
SEQ_ID_110  ------------------------------QEEVFDLFTDVHYSE-----------------------
SEQ_ID_111  -----------------------------RKVQEEVFDLFTDVH------------------------
SEQ_ID_112  ------------------------RSENAIVTSRKVQEE-----------------------------
SEQ_ID_113  -------------------------SENAIVTSRKVQEEV----------------------------
SEQ_ID_114  ----------------------------SRKVQEEVFDLFTDV-------------------------
SEQ_ID_115  ---------------------------TSRKVQEEVFDLFTD--------------------------
SEQ_ID_116  ---------------------------------VFDLFTDVHYSEVSA--------------------
SEQ_ID_117  -------------------------------VQEEVFDLFTDVHYS----------------------
SEQ_ID_118  --------------------------VTSRKVQEEVFDLFT---------------------------
SEQ_ID_119  ------------------------AIVTSRKVQ------------------------------------
SEQ_ID_120  -------------------------------EVFDLFTDV---------------------------
SEQ_ID_121  --------------------------------FTDVHYSEV--------------------------
SEQ_ID_122  ------------------------------------HYSEVSAKT----------------------
SEQ_ID_123  -------------------------IVTSRKVQE---------------------------------
SEQ_ID_124  --------------------------------LFTDVHYSE--------------------------
SEQ_ID_125  -------------------------NAIVTSRKV---------------------------------
SEQ_ID_126  ------------------------------VQEEVFDLF---------------------------
SEQ_ID_127  ---------------------------------------YSEVSAKTK------------------
SEQ_ID_128  ----------------------------------DVHYSEVSA-----------------------
SEQ_ID_129  --------------------KNAIVTSRK--------------------------------------
SEQ_ID_130  --------------------------------FDLFTDVHY-------------------------
SEQ_ID_131  ------------------KGRSENAIV----------------------------------------
SEQ_ID_132  ----------------------------KVQEEVFDL------------------------------
SEQ_ID_133  --------------------------------LFTDVHYSEV------------------------
SEQ_ID_134  -----------------------SENAIVTSR-----------------------------------
SEQ_ID_135  --------------------------TSRKVQEEV-------------------------------
SEQ_ID_136  ---------------------------------VHYSEVSAK------------------------
SEQ_ID_137  -----------------------SENAIVTSRKVQEEVFDLFTDVHYSEVSAKTK------------
SEQ_ID_138  ------------------KGRSENAIVTSRKVQEEVFDLFTDVHYSEVSAKTK--------------

RABLmaj 281  LLRNSVGDWENIQIPDGTPPSEVFAHTVLPEHSGAKCPTGASAGTFSAPQLDPAATKTPPAAVPRDSPTR
RABLmaj 351  GSLQPPPRTTPAPPAASWRSTEAISFDLSPTQFSSKAGFSPABGSDGAIGKSGGDSAPQRVGSGSGDSPV
RABLmaj 421  DGSSTRLPTPRGNLARAVDAGGVHLDLTAGSTKQSTGPNRKEDPKARKEREQTEMRAVLSCAGQRKVNPN
RABLmaj 491  GGGTDTGRSAAWLQNDADPMENNITLGLKKAGDAPSAARPAPVSSILDSHGVQGRCKGNQGTRGRDSDDD
RABLmaj 561  DDGARMQLQLKKPYAQIEHDIPQNAAAANQPAKRAKEKTRAKGRCRCCVL
```

FIG. 2C

```
PSA_Linf   1  MALCVRRLVLAATLAAVVALLLCTSSAPVARAAVKDDFTAAQRTNTLAVL
PSA_Linf  51  EAFGRAIPELGKLWKGDDFCPWESVVCDVTEVYLWEIGATYTGTLPEMFV
PSA_Linf 101  DVDYTAVMVKHLDFSQMGLGLSGTLPDSWSRLQGLTSLTLSGCGVSGTLP
PSA_Linf 151  PSWRSMKSLVSLWIESCESVTGKLPPEWSSMKSLRDLHLNGAKVSGTLPP
PSA_Linf 201  EWSTMKSLTLLDLQDTQVTGSLPPEWSSMKSMTILSLNGAKVSGTLPPQW
PSA_Linf 251  SSMTSLSLLSLEGTQLSGTLPPQWSGMTSLVTLFLQGTQVSGTLPPQWRS
PSA_Linf 301  MLNAEFLQLENCDLSGCLPPEWAAMPKLRHVELKGNQFAGCVPDSWAQKA
PSA_Linf 351  GLVVEIEDKHTGNSCIAGADCATTTTTTEPTSTASPTATPTSAPETECE PSA_Linf 401  VDGCEVCDGDSAARCAPCREGYFLTDEKTCLVYRDGGVVAVSIGAAAAAV
SEQ_ID_139    ------------------EGYFLTDEKTSLVYG-----------------
SEQ_ID_140    ----------------------FLTDEKTSLVYGDGG-------------
SEQ_ID_141    -------------------GEGYFLTDEKTSLVY----------------
SEQ_ID_142    --------------------GYFLTDEKTSLVYGD---------------
SEQ_ID_143    ----------------RSGEGYFLTDEKTSL-------------------
SEQ_ID_144    -----------------SGEGYFLTDEKTSLV------------------
SEQ_ID_145    ---------------------YFLTDEKTSLVYGDG--------------
SEQ_ID_146    ----------------------FLTDEKTSL-------------------
SEQ_ID_147    --------------------GYFLTDEKT---------------------
SEQ_ID_148    ------------------------LTDEKTSLV-----------------
SEQ_ID_149    ----------------RSGEGYFLT-------------------------
SEQ_ID_150    ---------------------YFLTDEKTS--------------------
SEQ_ID_151    -------------ARSARSGEGY---------------------------
SEQ_ID_152    --------------ARSGEGYFL---------------------------
SEQ_ID_153    ----------------------FLTDEKTSLV------------------
SEQ_ID_154    ------------------------LTDEKTSLVY----------------
SEQ_ID_155    --------------RSARSGEGY---------------------------
SEQ_ID_156    --------------RSARSGEGYF--------------------------
SEQ_ID_157    ----------KAARSARSGEGYFLTDEKTSLVYGDGG-------------

PSA_Linf 451  VCMAVLLSVGLAA
```

| Individuals | NS 5 days | PHA | SLA | NS 10 days | Pool A | Pool B | Pool C | Pool D | Pool E | Pool F | Pool G |
|---|---|---|---|---|---|---|---|---|---|---|---|
| | | | | | [IFN-g] pg/ml | | | | | | |
| Cured CL 1 | 57.41 | 2086.91 | 1884.33 | 4.79 | 1351.62 | 1399.88 | 1063.66 | 203.34 | 1420.49 | 25.54 | 1169.68 |
| Cured CL 2 | 0.00 | 3047.16 | 2862.15 | 256.29 | ND | 1779.32 | ND | 639.97 | ND | 854.75 | 0.00 |
| Cured CL 3 | 0.00 | 2852.42 | 2941.28 | 6.82 | ND | 1549.70 | ND | 0.00 | 1663.82 | 31.16 | 949.77 |
| Cured CL 4 | 4.13 | 2715.76 | 2524.83 | 351.34 | 254.44 | 1040.77 | ND | ND | 0.00 | 616.94 | 794.08 |
| Cured CL 5 | 0.00 | 3816.03 | 3684.93 | 158.51 | ND | 2591.46 | ND | 0.00 | 2727.18 | 0.00 | ND |
| Cured CL 6 | 51.19 | 2025.41 | 1769.70 | 56.26 | 46.25 | 58.96 | 1260.39 | 17.63 | 177.98 | ND | 143.42 |
| Naïve 1 | 0.00 | 2017.56 | 10.39 | 0.89 | 7.36 | 2.75 | 3.57 | 0.00 | ND | 17.54 | 2.58 |
| Naïve 2 | 1.20 | 2073.19 | 3.88 | 0.00 | 0.00 | 0.00 | 2.77 | 0.00 | 0.01 | 1.73 | 0.00 |
| Naïve 3 | 0.83 | 820.03 | 88.64 | 0.07 | 0.00 | 0.35 | 0.00 | 1.48 | ND | 3.29 | ND |
| Naïve 4 | 0.00 | 1180.94 | 0.00 | 0.00 | 0.00 | 0.00 | 0.00 | 0.00 | 1.08 | 0.00 | 3.65 |
| Naïve 5 | 0.22 | 2217.52 | 0.00 | 0.00 | 28.24 | 23.65 | ND | 17.27 | 26.67 | 2.74 | ND |
| Naïve 6 | 0.00 | 2117.05 | 0.00 | 0.00 | ND | 32.34 | 0.00 | 0.00 | 0.00 | 0.00 | 2.55 |

FIG. 4

SEQUENCE LISTING

```
<160> NUMBER OF SEQ ID NOS: 190

<210> SEQ ID NO 1
<211> LENGTH: 9
<212> TYPE: PRT
<213> ORGANISM: Leishmania major

<400> SEQUENCE: 1

Ala Ile Asn Ala Gln Met Ser Met Met
1               5

<210> SEQ ID NO 2
<211> LENGTH: 10
<212> TYPE: PRT
<213> ORGANISM: Leishmania major

<400> SEQUENCE: 2

Ile Lys Ala Ile Asn Ala Gln Met Ser Met
1               5                   10
```

```
<210> SEQ ID NO 3
<211> LENGTH: 9
<212> TYPE: PRT
<213> ORGANISM: Leishmania major

<400> SEQUENCE: 3

Lys Ala Ile Asn Ala Gln Met Ser Met
1               5

<210> SEQ ID NO 4
<211> LENGTH: 10
<212> TYPE: PRT
<213> ORGANISM: Leishmania major

<400> SEQUENCE: 4

Lys Ala Ile Asn Ala Gln Met Ser Met Met
1               5                   10

<210> SEQ ID NO 5
<211> LENGTH: 9
<212> TYPE: PRT
<213> ORGANISM: Leishmania major

<400> SEQUENCE: 5

Met Met Glu Arg Ile Cys Thr Glu Ala
1               5

<210> SEQ ID NO 6
<211> LENGTH: 9
<212> TYPE: PRT
<213> ORGANISM: Leishmania major

<400> SEQUENCE: 6

Met Glu Arg Ile Cys Thr Glu Ala Ala
1               5

<210> SEQ ID NO 7
<211> LENGTH: 10
<212> TYPE: PRT
<213> ORGANISM: Leishmania major

<400> SEQUENCE: 7

Met Met Glu Arg Ile Cys Thr Glu Ala Ala
1               5                   10

<210> SEQ ID NO 8
<211> LENGTH: 9
<212> TYPE: PRT
<213> ORGANISM: Leishmania major

<400> SEQUENCE: 8

Met Ser His Arg Thr Met Lys Ile Lys
1               5

<210> SEQ ID NO 9
<211> LENGTH: 10
<212> TYPE: PRT
<213> ORGANISM: Leishmania major

<400> SEQUENCE: 9

Met Ser His Arg Thr Met Lys Ile Lys Ala
1               5                   10

<210> SEQ ID NO 10
<211> LENGTH: 9
```

```
<212> TYPE: PRT
<213> ORGANISM: Leishmania major

<400> SEQUENCE: 10

Met Ser His Arg Thr Met Lys Ser Met
1               5

<210> SEQ ID NO 11
<211> LENGTH: 8
<212> TYPE: PRT
<213> ORGANISM: Leishmania major

<400> SEQUENCE: 11

Met Ser Met Ser His Arg Thr Met
1               5

<210> SEQ ID NO 12
<211> LENGTH: 9
<212> TYPE: PRT
<213> ORGANISM: Leishmania major

<400> SEQUENCE: 12

Met Ser Met Ser His Arg Thr Met Lys
1               5

<210> SEQ ID NO 13
<211> LENGTH: 10
<212> TYPE: PRT
<213> ORGANISM: Leishmania major

<400> SEQUENCE: 13

Met Ser Met Ser His Arg Thr Met Lys Ser
1               5                   10

<210> SEQ ID NO 14
<211> LENGTH: 9
<212> TYPE: PRT
<213> ORGANISM: Leishmania major

<400> SEQUENCE: 14

Asn Ala Gln Met Ser Met Met Glu Arg
1               5

<210> SEQ ID NO 15
<211> LENGTH: 8
<212> TYPE: PRT
<213> ORGANISM: Leishmania major

<400> SEQUENCE: 15

Ser Met Ser His Arg Thr Met Lys
1               5

<210> SEQ ID NO 16
<211> LENGTH: 9
<212> TYPE: PRT
<213> ORGANISM: Leishmania major

<400> SEQUENCE: 16

Ser Met Ser His Arg Thr Met Lys Ile
1               5

<210> SEQ ID NO 17
<211> LENGTH: 10
<212> TYPE: PRT
<213> ORGANISM: Leishmania major
```

```
<400> SEQUENCE: 17

Ser Met Ser His Arg Thr Met Lys Ile Lys
1               5                   10

<210> SEQ ID NO 18
<211> LENGTH: 9
<212> TYPE: PRT
<213> ORGANISM: Leishmania major

<400> SEQUENCE: 18

Ser Met Ser His Arg Thr Met Lys Ser
1               5

<210> SEQ ID NO 19
<211> LENGTH: 10
<212> TYPE: PRT
<213> ORGANISM: Leishmania major

<400> SEQUENCE: 19

Ser Met Ser His Arg Thr Met Lys Ser Met
1               5                   10

<210> SEQ ID NO 20
<211> LENGTH: 9
<212> TYPE: PRT
<213> ORGANISM: Leishmania major

<400> SEQUENCE: 20

Thr Met Lys Ser Met Ser His Arg Thr
1               5

<210> SEQ ID NO 21
<211> LENGTH: 10
<212> TYPE: PRT
<213> ORGANISM: Leishmania major

<400> SEQUENCE: 21

Thr Met Lys Ser Met Ser His Arg Thr Met
1               5                   10

<210> SEQ ID NO 22
<211> LENGTH: 35
<212> TYPE: PRT
<213> ORGANISM: Leishmania major

<400> SEQUENCE: 22

Ser Met Ser His Arg Thr Met Lys Ser Met Ser His Arg Thr Met Lys
1               5                   10                  15

Ile Lys Ala Ile Asn Ala Gln Met Ser Met Met Glu Arg Ile Cys Thr
            20                  25                  30

Glu Ala Ala
        35

<210> SEQ ID NO 23
<211> LENGTH: 40
<212> TYPE: PRT
<213> ORGANISM: Leishmania major

<400> SEQUENCE: 23

Lys Ala Arg Tyr Met Ser Met Ser His Arg Thr Met Lys Ser Met Ser
1               5                   10                  15

His Arg Thr Met Lys Ile Lys Ala Ile Asn Ala Gln Met Ser Met Met
```

Glu Arg Ile Cys Thr Glu Ala Ala
    35               40

<210> SEQ ID NO 24
<211> LENGTH: 15
<212> TYPE: PRT
<213> ORGANISM: Leishmania major

<400> SEQUENCE: 24

Arg Lys Pro Lys Arg Ser Trp Asn Val Tyr Val Gly Arg Ser Leu
1             5                   10               15

<210> SEQ ID NO 25
<211> LENGTH: 15
<212> TYPE: PRT
<213> ORGANISM: Leishmania major

<400> SEQUENCE: 25

Lys Pro Lys Arg Ser Trp Asn Val Tyr Val Gly Arg Ser Leu Lys
1             5                   10               15

<210> SEQ ID NO 26
<211> LENGTH: 15
<212> TYPE: PRT
<213> ORGANISM: Leishmania major

<400> SEQUENCE: 26

Pro Lys Arg Ser Trp Asn Val Tyr Val Gly Arg Ser Leu Lys Ala
1             5                   10               15

<210> SEQ ID NO 27
<211> LENGTH: 15
<212> TYPE: PRT
<213> ORGANISM: Leishmania major

<400> SEQUENCE: 27

Lys Arg Ser Trp Asn Val Tyr Val Gly Arg Ser Leu Lys Ala Ile
1             5                   10               15

<210> SEQ ID NO 28
<211> LENGTH: 15
<212> TYPE: PRT
<213> ORGANISM: Leishmania major

<400> SEQUENCE: 28

Arg Ser Trp Asn Val Tyr Val Gly Arg Ser Leu Lys Ala Ile Asn
1             5                   10               15

<210> SEQ ID NO 29
<211> LENGTH: 15
<212> TYPE: PRT
<213> ORGANISM: Leishmania major

<400> SEQUENCE: 29

Ser Trp Asn Val Tyr Val Gly Arg Ser Leu Lys Ala Ile Asn Ala
1             5                   10               15

<210> SEQ ID NO 30
<211> LENGTH: 15
<212> TYPE: PRT
<213> ORGANISM: Leishmania major

<400> SEQUENCE: 30

Trp Asn Val Tyr Val Gly Arg Ser Leu Lys Ala Ile Asn Ala Gln
1               5                   10                  15

<210> SEQ ID NO 31
<211> LENGTH: 15
<212> TYPE: PRT
<213> ORGANISM: Leishmania major

<400> SEQUENCE: 31

Asn Val Tyr Val Gly Arg Ser Leu Lys Ala Ile Asn Ala Gln Met
1               5                   10                  15

<210> SEQ ID NO 32
<211> LENGTH: 15
<212> TYPE: PRT
<213> ORGANISM: Leishmania major

<400> SEQUENCE: 32

Val Tyr Val Gly Arg Ser Leu Lys Ala Ile Asn Ala Gln Met Ser
1               5                   10                  15

<210> SEQ ID NO 33
<211> LENGTH: 15
<212> TYPE: PRT
<213> ORGANISM: Leishmania major

<400> SEQUENCE: 33

Tyr Val Gly Arg Ser Leu Lys Ala Ile Asn Ala Gln Met Ser Met
1               5                   10                  15

<210> SEQ ID NO 34
<211> LENGTH: 15
<212> TYPE: PRT
<213> ORGANISM: Leishmania major

<400> SEQUENCE: 34

Val Gly Arg Ser Leu Lys Ala Ile Asn Ala Gln Met Ser Met Ser
1               5                   10                  15

<210> SEQ ID NO 35
<211> LENGTH: 15
<212> TYPE: PRT
<213> ORGANISM: Leishmania major

<400> SEQUENCE: 35

Gly Arg Ser Leu Lys Ala Ile Asn Ala Gln Met Ser Met Ser His
1               5                   10                  15

<210> SEQ ID NO 36
<211> LENGTH: 15
<212> TYPE: PRT
<213> ORGANISM: Leishmania major

<400> SEQUENCE: 36

Arg Ser Leu Lys Ala Ile Asn Ala Gln Met Ser Met Ser His Arg
1               5                   10                  15

<210> SEQ ID NO 37
<211> LENGTH: 15
<212> TYPE: PRT
<213> ORGANISM: Leishmania major

<400> SEQUENCE: 37

Ser Leu Lys Ala Ile Asn Ala Gln Met Ser Met Ser His Arg Thr
1               5                   10                  15

```
<210> SEQ ID NO 38
<211> LENGTH: 15
<212> TYPE: PRT
<213> ORGANISM: Leishmania major

<400> SEQUENCE: 38

Leu Lys Ala Ile Asn Ala Gln Met Ser Met Ser His Arg Thr Met
1               5                   10                  15

<210> SEQ ID NO 39
<211> LENGTH: 15
<212> TYPE: PRT
<213> ORGANISM: Leishmania major

<400> SEQUENCE: 39

Lys Ala Ile Asn Ala Gln Met Ser Met Ser His Arg Thr Met Lys
1               5                   10                  15

<210> SEQ ID NO 40
<211> LENGTH: 15
<212> TYPE: PRT
<213> ORGANISM: Leishmania major

<400> SEQUENCE: 40

Ala Ile Asn Ala Gln Met Ser Met Ser His Arg Thr Met Lys Ile
1               5                   10                  15

<210> SEQ ID NO 41
<211> LENGTH: 15
<212> TYPE: PRT
<213> ORGANISM: Leishmania major

<400> SEQUENCE: 41

Ile Asn Ala Gln Met Ser Met Ser His Arg Thr Met Lys Ile Val
1               5                   10                  15

<210> SEQ ID NO 42
<211> LENGTH: 9
<212> TYPE: PRT
<213> ORGANISM: Leishmania major

<400> SEQUENCE: 42

Ala Gln Met Ser Met Ser His Arg Thr
1               5

<210> SEQ ID NO 43
<211> LENGTH: 9
<212> TYPE: PRT
<213> ORGANISM: Leishmania major

<400> SEQUENCE: 43

Gly Arg Ser Leu Lys Ala Ile Asn Ala
1               5

<210> SEQ ID NO 44
<211> LENGTH: 9
<212> TYPE: PRT
<213> ORGANISM: Leishmania major

<400> SEQUENCE: 44

Ile Asn Ala Gln Met Ser Met Ser His
1               5
```

```
<210> SEQ ID NO 45
<211> LENGTH: 9
<212> TYPE: PRT
<213> ORGANISM: Leishmania major

<400> SEQUENCE: 45

Leu Lys Ala Ile Asn Ala Gln Met Ser
1               5

<210> SEQ ID NO 46
<211> LENGTH: 9
<212> TYPE: PRT
<213> ORGANISM: Leishmania major

<400> SEQUENCE: 46

Asn Ala Gln Met Ser Met Ser His Arg
1               5

<210> SEQ ID NO 47
<211> LENGTH: 9
<212> TYPE: PRT
<213> ORGANISM: Leishmania major

<400> SEQUENCE: 47

Asn Val Tyr Val Gly Arg Ser Leu Lys
1               5

<210> SEQ ID NO 48
<211> LENGTH: 9
<212> TYPE: PRT
<213> ORGANISM: Leishmania major

<400> SEQUENCE: 48

Pro Lys Arg Ser Trp Asn Val Tyr Val
1               5

<210> SEQ ID NO 49
<211> LENGTH: 9
<212> TYPE: PRT
<213> ORGANISM: Leishmania major

<400> SEQUENCE: 49

Gln Met Ser Met Ser His Arg Thr Met
1               5

<210> SEQ ID NO 50
<211> LENGTH: 9
<212> TYPE: PRT
<213> ORGANISM: Leishmania major

<400> SEQUENCE: 50

Ser Leu Lys Ala Ile Asn Ala Gln Met
1               5

<210> SEQ ID NO 51
<211> LENGTH: 9
<212> TYPE: PRT
<213> ORGANISM: Leishmania major

<400> SEQUENCE: 51

Val Gly Arg Ser Leu Lys Ala Ile Asn
1               5

<210> SEQ ID NO 52
<211> LENGTH: 9
```

```
<212> TYPE: PRT
<213> ORGANISM: Leishmania major

<400> SEQUENCE: 52

Val Tyr Val Gly Arg Ser Leu Lys Ala
1               5

<210> SEQ ID NO 53
<211> LENGTH: 9
<212> TYPE: PRT
<213> ORGANISM: Leishmania major

<400> SEQUENCE: 53

Trp Asn Val Tyr Val Gly Arg Ser Leu
1               5

<210> SEQ ID NO 54
<211> LENGTH: 9
<212> TYPE: PRT
<213> ORGANISM: Leishmania major

<400> SEQUENCE: 54

Tyr Val Gly Arg Ser Leu Lys Ala Ile
1               5

<210> SEQ ID NO 55
<211> LENGTH: 10
<212> TYPE: PRT
<213> ORGANISM: Leishmania major

<400> SEQUENCE: 55

Ala Gln Met Ser Met Ser His Arg Thr Met
1               5                   10

<210> SEQ ID NO 56
<211> LENGTH: 10
<212> TYPE: PRT
<213> ORGANISM: Leishmania major

<400> SEQUENCE: 56

Lys Pro Lys Arg Ser Trp Asn Val Tyr Val
1               5                   10

<210> SEQ ID NO 57
<211> LENGTH: 10
<212> TYPE: PRT
<213> ORGANISM: Leishmania major

<400> SEQUENCE: 57

Lys Arg Ser Trp Asn Val Tyr Val Gly Arg
1               5                   10

<210> SEQ ID NO 58
<211> LENGTH: 10
<212> TYPE: PRT
<213> ORGANISM: Leishmania major

<400> SEQUENCE: 58

Leu Lys Ala Ile Asn Ala Gln Met Ser Met
1               5                   10

<210> SEQ ID NO 59
<211> LENGTH: 10
<212> TYPE: PRT
<213> ORGANISM: Leishmania major
```

-continued

```
<400> SEQUENCE: 59

Met Ser Met Ser His Arg Thr Met Lys Ile
1               5                   10

<210> SEQ ID NO 60
<211> LENGTH: 10
<212> TYPE: PRT
<213> ORGANISM: Leishmania major

<400> SEQUENCE: 60

Gln Met Ser Met Ser His Arg Thr Met Lys
1               5                   10

<210> SEQ ID NO 61
<211> LENGTH: 10
<212> TYPE: PRT
<213> ORGANISM: Leishmania major

<400> SEQUENCE: 61

Arg Ser Leu Lys Ala Ile Asn Ala Gln Met
1               5                   10

<210> SEQ ID NO 62
<211> LENGTH: 9
<212> TYPE: PRT
<213> ORGANISM: Leishmania major

<400> SEQUENCE: 62

Arg Ser Trp Asn Val Tyr Val Gly Arg
1               5

<210> SEQ ID NO 63
<211> LENGTH: 10
<212> TYPE: PRT
<213> ORGANISM: Leishmania major

<400> SEQUENCE: 63

Val Tyr Val Gly Arg Ser Leu Lys Ala Ile
1               5                   10

<210> SEQ ID NO 64
<211> LENGTH: 10
<212> TYPE: PRT
<213> ORGANISM: Leishmania major

<400> SEQUENCE: 64

Trp Asn Val Tyr Val Gly Arg Ser Leu Lys
1               5                   10

<210> SEQ ID NO 65
<211> LENGTH: 31
<212> TYPE: PRT
<213> ORGANISM: Leishmania major

<400> SEQUENCE: 65

Lys Pro Lys Arg Ser Trp Asn Val Tyr Val Gly Arg Ser Leu Lys Ala
1               5                   10                  15

Ile Asn Ala Gln Met Ser Met Ser His Arg Thr Met Lys Ile Val
            20                  25                  30

<210> SEQ ID NO 66
<211> LENGTH: 34
<212> TYPE: PRT
```

<213> ORGANISM: Leishmania major

<400> SEQUENCE: 66

Lys Gly Arg Lys Pro Lys Arg Ser Trp Asn Val Tyr Val Gly Arg Ser
1               5                   10                  15

Leu Lys Ala Ile Asn Ala Gln Met Ser Met Ser His Arg Thr Met Lys
            20                  25                  30

Ile Val

<210> SEQ ID NO 67
<211> LENGTH: 9
<212> TYPE: PRT
<213> ORGANISM: Leishmania major

<400> SEQUENCE: 67

Met Glu Asn Asn Ile Thr Gly Gly Leu
1               5

<210> SEQ ID NO 68
<211> LENGTH: 9
<212> TYPE: PRT
<213> ORGANISM: Leishmania major

<400> SEQUENCE: 68

Lys Thr Lys Gln His Leu Arg Glu Met
1               5

<210> SEQ ID NO 69
<211> LENGTH: 25
<212> TYPE: PRT
<213> ORGANISM: Leishmania major

<400> SEQUENCE: 69

Lys Ala Arg Tyr Met Glu Asn Asn Ile Thr Gly Gly Leu Ala Arg Tyr
1               5                   10                  15

Lys Thr Lys Gln His Val Arg Glu Met
            20                  25

<210> SEQ ID NO 70
<211> LENGTH: 9
<212> TYPE: PRT
<213> ORGANISM: Leishmania major

<400> SEQUENCE: 70

Arg Phe Ala Gln Gly Glu His Asp Ile
1               5

<210> SEQ ID NO 71
<211> LENGTH: 9
<212> TYPE: PRT
<213> ORGANISM: Leishmania major

<400> SEQUENCE: 71

Arg Leu Pro Glu Asn Ala Phe Val Ile
1               5

<210> SEQ ID NO 72
<211> LENGTH: 9
<212> TYPE: PRT
<213> ORGANISM: Leishmania major

<400> SEQUENCE: 72

Thr Gln Gly Ser Ser Lys Ala Gly Phe

```
<210> SEQ ID NO 73
<211> LENGTH: 34
<212> TYPE: PRT
<213> ORGANISM: Leishmania major

<400> SEQUENCE: 73

Lys Ala Arg Tyr Arg Phe Ala Gln Gly Glu His Asp Ile Arg Leu Pro
1               5                   10                  15

Glu Asn Ala Phe Val Ile Ala Arg Tyr Thr Gln Gly Ser Ser Lys Ala
            20                  25                  30

Gly Phe

<210> SEQ ID NO 74
<211> LENGTH: 9
<212> TYPE: PRT
<213> ORGANISM: Leishmania major

<400> SEQUENCE: 74

Met Pro His Val Asp Gln Ser Ser Ile
1               5

<210> SEQ ID NO 75
<211> LENGTH: 9
<212> TYPE: PRT
<213> ORGANISM: Leishmania major

<400> SEQUENCE: 75

Ala Ser Phe Arg Ser Thr Glu Ala Ile
1               5

<210> SEQ ID NO 76
<211> LENGTH: 9
<212> TYPE: PRT
<213> ORGANISM: Leishmania major

<400> SEQUENCE: 76

Ser Ser Ile Met Val Val Ala Asn Lys
1               5

<210> SEQ ID NO 77
<211> LENGTH: 36
<212> TYPE: PRT
<213> ORGANISM: Leishmania major

<400> SEQUENCE: 77

Lys Ala Arg Tyr Met Pro His Val Asp Gln Ser Ser Ile Ala Arg Tyr
1               5                   10                  15

Ala Ser Phe Arg Ser Thr Glu Ala Ile Arg Tyr Ser Ser Ile Met Val
            20                  25                  30

Val Ala Asn Lys
            35

<210> SEQ ID NO 78
<211> LENGTH: 15
<212> TYPE: PRT
<213> ORGANISM: Leishmania major

<400> SEQUENCE: 78

Lys Gly Arg Leu His Ser Val Val Gly Arg His Leu Ser Ile Val
1               5                   10                  15
```

-continued

<210> SEQ ID NO 79
<211> LENGTH: 15
<212> TYPE: PRT
<213> ORGANISM: Leishmania major

<400> SEQUENCE: 79

Gly Arg Leu His Ser Val Val Gly Arg His Leu Ser Ile Val Ala
1               5                   10                  15

<210> SEQ ID NO 80
<211> LENGTH: 15
<212> TYPE: PRT
<213> ORGANISM: Leishmania major

<400> SEQUENCE: 80

Arg Leu His Ser Val Val Gly Arg His Leu Ser Ile Val Ala Asp
1               5                   10                  15

<210> SEQ ID NO 81
<211> LENGTH: 15
<212> TYPE: PRT
<213> ORGANISM: Leishmania major

<400> SEQUENCE: 81

Leu His Ser Val Val Gly Arg His Leu Ser Ile Val Ala Asp His
1               5                   10                  15

<210> SEQ ID NO 82
<211> LENGTH: 15
<212> TYPE: PRT
<213> ORGANISM: Leishmania major

<400> SEQUENCE: 82

His Ser Val Val Gly Arg His Leu Ser Ile Val Ala Asp His Met
1               5                   10                  15

<210> SEQ ID NO 83
<211> LENGTH: 15
<212> TYPE: PRT
<213> ORGANISM: Leishmania major

<400> SEQUENCE: 83

Ser Val Val Gly Arg His Leu Ser Ile Val Ala Asp His Met Pro
1               5                   10                  15

<210> SEQ ID NO 84
<211> LENGTH: 15
<212> TYPE: PRT
<213> ORGANISM: Leishmania major

<400> SEQUENCE: 84

Val Val Gly Arg His Leu Ser Ile Val Ala Asp His Met Pro His
1               5                   10                  15

<210> SEQ ID NO 85
<211> LENGTH: 15
<212> TYPE: PRT
<213> ORGANISM: Leishmania major

<400> SEQUENCE: 85

Val Gly Arg His Leu Ser Ile Val Ala Asp His Met Pro His Leu
1               5                   10                  15

<210> SEQ ID NO 86

-continued

```
<211> LENGTH: 15
<212> TYPE: PRT
<213> ORGANISM: Leishmania major

<400> SEQUENCE: 86

Gly Arg His Leu Ser Ile Val Ala Asp His Met Pro His Leu Asp
1               5                   10                  15

<210> SEQ ID NO 87
<211> LENGTH: 15
<212> TYPE: PRT
<213> ORGANISM: Leishmania major

<400> SEQUENCE: 87

Arg His Leu Ser Ile Val Ala Asp His Met Pro His Leu Asp Gln
1               5                   10                  15

<210> SEQ ID NO 88
<211> LENGTH: 9
<212> TYPE: PRT
<213> ORGANISM: Leishmania major

<400> SEQUENCE: 88

His Leu Ser Ile Val Ala Asp His Met
1               5

<210> SEQ ID NO 89
<211> LENGTH: 9
<212> TYPE: PRT
<213> ORGANISM: Leishmania major

<400> SEQUENCE: 89

Ile Val Ala Asp His Met Pro His Leu
1               5

<210> SEQ ID NO 90
<211> LENGTH: 9
<212> TYPE: PRT
<213> ORGANISM: Leishmania major

<400> SEQUENCE: 90

Leu His Ser Val Val Gly Arg His Leu
1               5

<210> SEQ ID NO 91
<211> LENGTH: 9
<212> TYPE: PRT
<213> ORGANISM: Leishmania major

<400> SEQUENCE: 91

Val Gly Arg His Leu Ser Ile Val Ala
1               5

<210> SEQ ID NO 92
<211> LENGTH: 9
<212> TYPE: PRT
<213> ORGANISM: Leishmania major

<400> SEQUENCE: 92

Lys Gly Arg Leu His Ser Val Val Gly
1               5

<210> SEQ ID NO 93
<211> LENGTH: 9
<212> TYPE: PRT
```

<213> ORGANISM: Leishmania major

<400> SEQUENCE: 93

Arg Leu His Ser Val Val Gly Arg His
1               5

<210> SEQ ID NO 94
<211> LENGTH: 9
<212> TYPE: PRT
<213> ORGANISM: Leishmania major

<400> SEQUENCE: 94

Ser Val Val Gly Arg His Leu Ser Ile
1               5

<210> SEQ ID NO 95
<211> LENGTH: 9
<212> TYPE: PRT
<213> ORGANISM: Leishmania major

<400> SEQUENCE: 95

Val Val Gly Arg His Leu Ser Ile Val
1               5

<210> SEQ ID NO 96
<211> LENGTH: 21
<212> TYPE: PRT
<213> ORGANISM: Leishmania major

<400> SEQUENCE: 96

Leu His Ser Val Val Gly Arg His Leu Ser Ile Val Ala Asp His Met
1               5                   10                  15

Pro His Leu Asp Gln
            20

<210> SEQ ID NO 97
<211> LENGTH: 24
<212> TYPE: PRT
<213> ORGANISM: Leishmania major

<400> SEQUENCE: 97

Lys Gly Arg Leu His Ser Val Val Gly Arg His Leu Ser Ile Val Ala
1               5                   10                  15

Asp His Met Pro His Leu Asp Gln
            20

<210> SEQ ID NO 98
<211> LENGTH: 15
<212> TYPE: PRT
<213> ORGANISM: Leishmania major

<400> SEQUENCE: 98

Ala Ile Val Thr Ser Arg Lys Val Gln Glu Glu Val Phe Asp Leu
1               5                   10                  15

<210> SEQ ID NO 99
<211> LENGTH: 15
<212> TYPE: PRT
<213> ORGANISM: Leishmania major

<400> SEQUENCE: 99

Asp Leu Phe Thr Asp Val His Tyr Ser Glu Val Ser Ala Lys Thr
1               5                   10                  15

-continued

<210> SEQ ID NO 100
<211> LENGTH: 15
<212> TYPE: PRT
<213> ORGANISM: Leishmania major

<400> SEQUENCE: 100

Glu Glu Val Phe Asp Leu Phe Thr Asp Val His Tyr Ser Glu Val
1               5                   10                  15

<210> SEQ ID NO 101
<211> LENGTH: 15
<212> TYPE: PRT
<213> ORGANISM: Leishmania major

<400> SEQUENCE: 101

Glu Asn Ala Ile Val Thr Ser Arg Lys Val Gln Glu Glu Val Phe
1               5                   10                  15

<210> SEQ ID NO 102
<211> LENGTH: 15
<212> TYPE: PRT
<213> ORGANISM: Leishmania major

<400> SEQUENCE: 102

Glu Val Phe Asp Leu Phe Thr Asp Val His Tyr Ser Glu Val Ser
1               5                   10                  15

<210> SEQ ID NO 103
<211> LENGTH: 15
<212> TYPE: PRT
<213> ORGANISM: Leishmania major

<400> SEQUENCE: 103

Phe Asp Leu Phe Thr Asp Val His Tyr Ser Glu Val Ser Ala Lys
1               5                   10                  15

<210> SEQ ID NO 104
<211> LENGTH: 15
<212> TYPE: PRT
<213> ORGANISM: Leishmania major

<400> SEQUENCE: 104

Gly Arg Ser Glu Asn Ala Ile Val Thr Ser Arg Lys Val Gln Glu
1               5                   10                  15

<210> SEQ ID NO 105
<211> LENGTH: 15
<212> TYPE: PRT
<213> ORGANISM: Leishmania major

<400> SEQUENCE: 105

Ile Val Thr Ser Arg Lys Val Gln Glu Glu Val Phe Asp Leu Phe
1               5                   10                  15

<210> SEQ ID NO 106
<211> LENGTH: 15
<212> TYPE: PRT
<213> ORGANISM: Leishmania major

<400> SEQUENCE: 106

Lys Gly Arg Ser Glu Asn Ala Ile Val Thr Ser Arg Lys Val Gln
1               5                   10                  15

<210> SEQ ID NO 107

```
<211> LENGTH: 15
<212> TYPE: PRT
<213> ORGANISM: Leishmania major

<400> SEQUENCE: 107

Lys Val Gln Glu Glu Val Phe Asp Leu Phe Thr Asp Val His Tyr
 1               5                  10                  15

<210> SEQ ID NO 108
<211> LENGTH: 15
<212> TYPE: PRT
<213> ORGANISM: Leishmania major

<400> SEQUENCE: 108

Leu Phe Thr Asp Val His Tyr Ser Glu Val Ser Ala Lys Thr Lys
 1               5                  10                  15

<210> SEQ ID NO 109
<211> LENGTH: 15
<212> TYPE: PRT
<213> ORGANISM: Leishmania major

<400> SEQUENCE: 109

Asn Ala Ile Val Thr Ser Arg Lys Val Gln Glu Glu Val Phe Asp
 1               5                  10                  15

<210> SEQ ID NO 110
<211> LENGTH: 15
<212> TYPE: PRT
<213> ORGANISM: Leishmania major

<400> SEQUENCE: 110

Gln Glu Glu Val Phe Asp Leu Phe Thr Asp Val His Tyr Ser Glu
 1               5                  10                  15

<210> SEQ ID NO 111
<211> LENGTH: 15
<212> TYPE: PRT
<213> ORGANISM: Leishmania major

<400> SEQUENCE: 111

Arg Lys Val Gln Glu Glu Val Phe Asp Leu Phe Thr Asp Val His
 1               5                  10                  15

<210> SEQ ID NO 112
<211> LENGTH: 15
<212> TYPE: PRT
<213> ORGANISM: Leishmania major

<400> SEQUENCE: 112

Arg Ser Glu Asn Ala Ile Val Thr Ser Arg Lys Val Gln Glu Glu
 1               5                  10                  15

<210> SEQ ID NO 113
<211> LENGTH: 15
<212> TYPE: PRT
<213> ORGANISM: Leishmania major

<400> SEQUENCE: 113

Ser Glu Asn Ala Ile Val Thr Ser Arg Lys Val Gln Glu Glu Val
 1               5                  10                  15

<210> SEQ ID NO 114
<211> LENGTH: 15
<212> TYPE: PRT
```

<213> ORGANISM: Leishmania major

<400> SEQUENCE: 114

Ser Arg Lys Val Gln Glu Glu Val Phe Asp Leu Phe Thr Asp Val
1               5                   10                  15

<210> SEQ ID NO 115
<211> LENGTH: 15
<212> TYPE: PRT
<213> ORGANISM: Leishmania major

<400> SEQUENCE: 115

Thr Ser Arg Lys Val Gln Glu Glu Val Phe Asp Leu Phe Thr Asp
1               5                   10                  15

<210> SEQ ID NO 116
<211> LENGTH: 15
<212> TYPE: PRT
<213> ORGANISM: Leishmania major

<400> SEQUENCE: 116

Val Phe Asp Leu Phe Thr Asp Val His Tyr Ser Glu Val Ser Ala
1               5                   10                  15

<210> SEQ ID NO 117
<211> LENGTH: 15
<212> TYPE: PRT
<213> ORGANISM: Leishmania major

<400> SEQUENCE: 117

Val Gln Glu Glu Val Phe Asp Leu Phe Thr Asp Val His Tyr Ser
1               5                   10                  15

<210> SEQ ID NO 118
<211> LENGTH: 14
<212> TYPE: PRT
<213> ORGANISM: Leishmania major

<400> SEQUENCE: 118

Val Thr Ser Arg Lys Gln Glu Glu Val Phe Asp Leu Phe Thr
1               5                   10

<210> SEQ ID NO 119
<211> LENGTH: 9
<212> TYPE: PRT
<213> ORGANISM: Leishmania major

<400> SEQUENCE: 119

Ala Ile Val Thr Ser Arg Lys Val Gln
1               5

<210> SEQ ID NO 120
<211> LENGTH: 9
<212> TYPE: PRT
<213> ORGANISM: Leishmania major

<400> SEQUENCE: 120

Glu Val Phe Asp Leu Phe Thr Asp Val
1               5

<210> SEQ ID NO 121
<211> LENGTH: 9
<212> TYPE: PRT
<213> ORGANISM: Leishmania major

```
<400> SEQUENCE: 121

Phe Thr Asp Val His Tyr Ser Glu Val
1               5

<210> SEQ ID NO 122
<211> LENGTH: 9
<212> TYPE: PRT
<213> ORGANISM: Leishmania major

<400> SEQUENCE: 122

His Tyr Ser Glu Val Ser Ala Lys Thr
1               5

<210> SEQ ID NO 123
<211> LENGTH: 9
<212> TYPE: PRT
<213> ORGANISM: Leishmania major

<400> SEQUENCE: 123

Ile Val Thr Ser Arg Lys Val Gln Glu
1               5

<210> SEQ ID NO 124
<211> LENGTH: 9
<212> TYPE: PRT
<213> ORGANISM: Leishmania major

<400> SEQUENCE: 124

Leu Phe Thr Asp Val His Tyr Ser Glu
1               5

<210> SEQ ID NO 125
<211> LENGTH: 9
<212> TYPE: PRT
<213> ORGANISM: Leishmania major

<400> SEQUENCE: 125

Asn Ala Ile Val Thr Ser Arg Lys Val
1               5

<210> SEQ ID NO 126
<211> LENGTH: 9
<212> TYPE: PRT
<213> ORGANISM: Leishmania major

<400> SEQUENCE: 126

Val Gln Glu Glu Val Phe Asp Leu Phe
1               5

<210> SEQ ID NO 127
<211> LENGTH: 9
<212> TYPE: PRT
<213> ORGANISM: Leishmania major

<400> SEQUENCE: 127

Tyr Ser Glu Val Ser Ala Lys Thr Lys
1               5

<210> SEQ ID NO 128
<211> LENGTH: 9
<212> TYPE: PRT
<213> ORGANISM: Leishmania major

<400> SEQUENCE: 128
```

Asp Val His Tyr Ser Glu Val Ser Ala
1               5

<210> SEQ ID NO 129
<211> LENGTH: 9
<212> TYPE: PRT
<213> ORGANISM: Leishmania major

<400> SEQUENCE: 129

Glu Asn Ala Ile Val Thr Ser Arg Lys
1               5

<210> SEQ ID NO 130
<211> LENGTH: 9
<212> TYPE: PRT
<213> ORGANISM: Leishmania major

<400> SEQUENCE: 130

Phe Asp Leu Phe Thr Asp Val His Tyr
1               5

<210> SEQ ID NO 131
<211> LENGTH: 9
<212> TYPE: PRT
<213> ORGANISM: Leishmania major

<400> SEQUENCE: 131

Lys Gly Arg Ser Glu Asn Ala Ile Val
1               5

<210> SEQ ID NO 132
<211> LENGTH: 9
<212> TYPE: PRT
<213> ORGANISM: Leishmania major

<400> SEQUENCE: 132

Lys Val Gln Glu Glu Val Phe Asp Leu
1               5

<210> SEQ ID NO 133
<211> LENGTH: 10
<212> TYPE: PRT
<213> ORGANISM: Leishmania major

<400> SEQUENCE: 133

Leu Phe Thr Asp Val His Tyr Ser Glu Val
1               5                   10

<210> SEQ ID NO 134
<211> LENGTH: 9
<212> TYPE: PRT
<213> ORGANISM: Leishmania major

<400> SEQUENCE: 134

Ser Glu Asn Ala Ile Val Thr Ser Arg
1               5

<210> SEQ ID NO 135
<211> LENGTH: 9
<212> TYPE: PRT
<213> ORGANISM: Leishmania major

<400> SEQUENCE: 135

Thr Ser Arg Lys Val Gln Glu Glu Val
1               5

<210> SEQ ID NO 136
<211> LENGTH: 9
<212> TYPE: PRT
<213> ORGANISM: Leishmania major

<400> SEQUENCE: 136

Val His Tyr Ser Glu Val Ser Ala Lys
1               5

<210> SEQ ID NO 137
<211> LENGTH: 32
<212> TYPE: PRT
<213> ORGANISM: Leishmania major

<400> SEQUENCE: 137

Ser Glu Asn Ala Ile Val Thr Ser Arg Lys Val Gln Glu Glu Val Phe
1               5                   10                  15

Asp Leu Phe Thr Asp Val His Tyr Ser Glu Val Ser Ala Lys Thr Lys
            20                  25                  30

<210> SEQ ID NO 138
<211> LENGTH: 35
<212> TYPE: PRT
<213> ORGANISM: Leishmania major

<400> SEQUENCE: 138

Lys Gly Arg Ser Glu Asn Ala Ile Val Thr Ser Arg Lys Val Gln Glu
1               5                   10                  15

Glu Val Phe Asp Leu Phe Thr Asp Val His Tyr Ser Glu Val Ser Ala
            20                  25                  30

Lys Thr Lys
        35

<210> SEQ ID NO 139
<211> LENGTH: 15
<212> TYPE: PRT
<213> ORGANISM: Leishmania infantum

<400> SEQUENCE: 139

Glu Gly Tyr Phe Leu Thr Asp Glu Lys Thr Ser Leu Val Tyr Gly
1               5                   10                  15

<210> SEQ ID NO 140
<211> LENGTH: 15
<212> TYPE: PRT
<213> ORGANISM: Leishmania infantum

<400> SEQUENCE: 140

Phe Leu Thr Asp Glu Lys Thr Ser Leu Val Tyr Gly Asp Gly Gly
1               5                   10                  15

<210> SEQ ID NO 141
<211> LENGTH: 15
<212> TYPE: PRT
<213> ORGANISM: Leishmania infantum

<400> SEQUENCE: 141

Gly Glu Gly Tyr Phe Leu Thr Asp Glu Lys Thr Ser Leu Val Tyr
1               5                   10                  15

<210> SEQ ID NO 142
<211> LENGTH: 15

```
<212> TYPE: PRT
<213> ORGANISM: Leishmania infantum

<400> SEQUENCE: 142

Gly Tyr Phe Leu Thr Asp Glu Lys Thr Ser Leu Val Tyr Gly Asp
1               5                   10                  15

<210> SEQ ID NO 143
<211> LENGTH: 15
<212> TYPE: PRT
<213> ORGANISM: Leishmania infantum

<400> SEQUENCE: 143

Arg Ser Gly Glu Gly Tyr Phe Leu Thr Asp Glu Lys Thr Ser Leu
1               5                   10                  15

<210> SEQ ID NO 144
<211> LENGTH: 15
<212> TYPE: PRT
<213> ORGANISM: Leishmania infantum

<400> SEQUENCE: 144

Ser Gly Glu Gly Tyr Phe Leu Thr Asp Glu Lys Thr Ser Leu Val
1               5                   10                  15

<210> SEQ ID NO 145
<211> LENGTH: 15
<212> TYPE: PRT
<213> ORGANISM: Leishmania infantum

<400> SEQUENCE: 145

Tyr Phe Leu Thr Asp Glu Lys Thr Ser Leu Val Tyr Gly Asp Gly
1               5                   10                  15

<210> SEQ ID NO 146
<211> LENGTH: 9
<212> TYPE: PRT
<213> ORGANISM: Leishmania infantum

<400> SEQUENCE: 146

Phe Leu Thr Asp Glu Lys Thr Ser Leu
1               5

<210> SEQ ID NO 147
<211> LENGTH: 9
<212> TYPE: PRT
<213> ORGANISM: Leishmania infantum

<400> SEQUENCE: 147

Gly Tyr Phe Leu Thr Asp Glu Lys Thr
1               5

<210> SEQ ID NO 148
<211> LENGTH: 9
<212> TYPE: PRT
<213> ORGANISM: Leishmania infantum

<400> SEQUENCE: 148

Leu Thr Asp Glu Lys Thr Ser Leu Val
1               5

<210> SEQ ID NO 149
<211> LENGTH: 9
<212> TYPE: PRT
<213> ORGANISM: Leishmania infantum
```

<400> SEQUENCE: 149

Arg Ser Gly Glu Gly Tyr Phe Leu Thr
1               5

<210> SEQ ID NO 150
<211> LENGTH: 9
<212> TYPE: PRT
<213> ORGANISM: Leishmania infantum

<400> SEQUENCE: 150

Tyr Phe Leu Thr Asp Glu Lys Thr Ser
1               5

<210> SEQ ID NO 151
<211> LENGTH: 10
<212> TYPE: PRT
<213> ORGANISM: Leishmania infantum

<400> SEQUENCE: 151

Ala Arg Ser Ala Arg Ser Gly Glu Gly Tyr
1               5                   10

<210> SEQ ID NO 152
<211> LENGTH: 9
<212> TYPE: PRT
<213> ORGANISM: Leishmania infantum

<400> SEQUENCE: 152

Ala Arg Ser Gly Glu Gly Tyr Phe Leu
1               5

<210> SEQ ID NO 153
<211> LENGTH: 10
<212> TYPE: PRT
<213> ORGANISM: Leishmania infantum

<400> SEQUENCE: 153

Phe Leu Thr Asp Glu Lys Thr Ser Leu Val
1               5                   10

<210> SEQ ID NO 154
<211> LENGTH: 10
<212> TYPE: PRT
<213> ORGANISM: Leishmania infantum

<400> SEQUENCE: 154

Leu Thr Asp Glu Lys Thr Ser Leu Val Tyr
1               5                   10

<210> SEQ ID NO 155
<211> LENGTH: 9
<212> TYPE: PRT
<213> ORGANISM: Leishmania infantum

<400> SEQUENCE: 155

Arg Ser Ala Arg Ser Gly Glu Gly Tyr
1               5

<210> SEQ ID NO 156
<211> LENGTH: 10
<212> TYPE: PRT
<213> ORGANISM: Leishmania infantum

<400> SEQUENCE: 156

Arg Ser Ala Arg Ser Gly Glu Gly Tyr Phe
1               5                   10

<210> SEQ ID NO 157
<211> LENGTH: 27
<212> TYPE: PRT
<213> ORGANISM: Leishmania infantum

<400> SEQUENCE: 157

Lys Ala Ala Arg Ser Ala Arg Ser Gly Glu Gly Tyr Phe Leu Thr Asp
1               5                   10                  15

Glu Lys Thr Ser Leu Val Tyr Gly Asp Gly Gly
            20                  25

<210> SEQ ID NO 158
<211> LENGTH: 15
<212> TYPE: PRT
<213> ORGANISM: Leishmania infantum

<400> SEQUENCE: 158

Asp Tyr Ser His Ser Met Ile Arg Asp Leu Asp Phe Ser Asn Met
1               5                   10                  15

<210> SEQ ID NO 159
<211> LENGTH: 15
<212> TYPE: PRT
<213> ORGANISM: Leishmania infantum

<400> SEQUENCE: 159

Gly Ser Asp Tyr Ser His Ser Met Ile Arg Asp Leu Asp Phe Ser
1               5                   10                  15

<210> SEQ ID NO 160
<211> LENGTH: 15
<212> TYPE: PRT
<213> ORGANISM: Leishmania infantum

<400> SEQUENCE: 160

His Ser Met Ile Arg Asp Leu Asp Phe Ser Asn Met Gly Leu Leu
1               5                   10                  15

<210> SEQ ID NO 161
<211> LENGTH: 15
<212> TYPE: PRT
<213> ORGANISM: Leishmania infantum

<400> SEQUENCE: 161

Ile Arg Asp Leu Asp Phe Ser Asn Met Gly Leu Leu Leu Ser Gly
1               5                   10                  15

<210> SEQ ID NO 162
<211> LENGTH: 15
<212> TYPE: PRT
<213> ORGANISM: Leishmania infantum

<400> SEQUENCE: 162

Met Ile Arg Asp Leu Asp Phe Ser Asn Met Gly Leu Leu Leu Ser
1               5                   10                  15

<210> SEQ ID NO 163
<211> LENGTH: 15
<212> TYPE: PRT
<213> ORGANISM: Leishmania infantum

<400> SEQUENCE: 163

Met Pro Ser Gly Ser Asp Tyr Ser His Ser Met Ile Arg Asp Leu
1               5                   10                  15

<210> SEQ ID NO 164
<211> LENGTH: 15
<212> TYPE: PRT
<213> ORGANISM: Leishmania infantum

<400> SEQUENCE: 164

Pro Ser Gly Ser Asp Tyr Ser His Ser Met Ile Arg Asp Leu Asp
1               5                   10                  15

<210> SEQ ID NO 165
<211> LENGTH: 15
<212> TYPE: PRT
<213> ORGANISM: Leishmania infantum

<400> SEQUENCE: 165

Arg Asp Leu Asp Phe Ser Asn Met Gly Leu Leu Leu Ser Gly Thr
1               5                   10                  15

<210> SEQ ID NO 166
<211> LENGTH: 15
<212> TYPE: PRT
<213> ORGANISM: Leishmania infantum

<400> SEQUENCE: 166

Ser Asp Tyr Ser His Ser Met Ile Arg Asp Leu Asp Phe Ser Asn
1               5                   10                  15

<210> SEQ ID NO 167
<211> LENGTH: 15
<212> TYPE: PRT
<213> ORGANISM: Leishmania infantum

<400> SEQUENCE: 167

Ser Gly Ser Asp Tyr Ser His Ser Met Ile Arg Asp Leu Asp Phe
1               5                   10                  15

<210> SEQ ID NO 168
<211> LENGTH: 15
<212> TYPE: PRT
<213> ORGANISM: Leishmania infantum

<400> SEQUENCE: 168

Ser His Ser Met Ile Arg Asp Leu Asp Phe Ser Asn Met Gly Leu
1               5                   10                  15

<210> SEQ ID NO 169
<211> LENGTH: 15
<212> TYPE: PRT
<213> ORGANISM: Leishmania infantum

<400> SEQUENCE: 169

Ser Met Ile Arg Asp Leu Asp Phe Ser Asn Met Gly Leu Leu Leu
1               5                   10                  15

<210> SEQ ID NO 170
<211> LENGTH: 15
<212> TYPE: PRT
<213> ORGANISM: Leishmania infantum

<400> SEQUENCE: 170

```
Tyr Ser His Ser Met Ile Arg Asp Leu Asp Phe Ser Asn Met Gly
1               5                   10                  15

<210> SEQ ID NO 171
<211> LENGTH: 9
<212> TYPE: PRT
<213> ORGANISM: Leishmania infantum

<400> SEQUENCE: 171

Asp Phe Ser Asn Met Gly Leu Leu Leu
1               5

<210> SEQ ID NO 172
<211> LENGTH: 9
<212> TYPE: PRT
<213> ORGANISM: Leishmania infantum

<400> SEQUENCE: 172

Phe Ser Asn Met Gly Leu Leu Leu Ser
1               5

<210> SEQ ID NO 173
<211> LENGTH: 9
<212> TYPE: PRT
<213> ORGANISM: Leishmania infantum

<400> SEQUENCE: 173

His Ser Met Ile Arg Asp Leu Asp Phe
1               5

<210> SEQ ID NO 174
<211> LENGTH: 9
<212> TYPE: PRT
<213> ORGANISM: Leishmania infantum

<400> SEQUENCE: 174

Ile Arg Asp Leu Asp Phe Ser Asn Met
1               5

<210> SEQ ID NO 175
<211> LENGTH: 9
<212> TYPE: PRT
<213> ORGANISM: Leishmania infantum

<400> SEQUENCE: 175

Leu Asp Phe Ser Asn Met Gly Leu Leu
1               5

<210> SEQ ID NO 176
<211> LENGTH: 9
<212> TYPE: PRT
<213> ORGANISM: Leishmania infantum

<400> SEQUENCE: 176

Met Ile Arg Asp Leu Asp Phe Ser Asn
1               5

<210> SEQ ID NO 177
<211> LENGTH: 9
<212> TYPE: PRT
<213> ORGANISM: Leishmania infantum

<400> SEQUENCE: 177

Ser Asp Tyr Ser His Ser Met Ile Arg
1               5
```

<210> SEQ ID NO 178
<211> LENGTH: 9
<212> TYPE: PRT
<213> ORGANISM: Leishmania infantum

<400> SEQUENCE: 178

Tyr Ser His Ser Met Ile Arg Asp Leu
1               5

<210> SEQ ID NO 179
<211> LENGTH: 10
<212> TYPE: PRT
<213> ORGANISM: Leishmania infantum

<400> SEQUENCE: 179

Gly Ser Asp Tyr Ser His Ser Met Ile Arg
1               5                   10

<210> SEQ ID NO 180
<211> LENGTH: 9
<212> TYPE: PRT
<213> ORGANISM: Leishmania infantum

<400> SEQUENCE: 180

Lys Glu Met Pro Ser Gly Ser Asp Tyr
1               5

<210> SEQ ID NO 181
<211> LENGTH: 10
<212> TYPE: PRT
<213> ORGANISM: Leishmania infantum

<400> SEQUENCE: 181

Met Ile Arg Asp Leu Asp Phe Ser Asn Met
1               5                   10

<210> SEQ ID NO 182
<211> LENGTH: 9
<212> TYPE: PRT
<213> ORGANISM: Leishmania infantum

<400> SEQUENCE: 182

Met Pro Ser Gly Ser Asp Tyr Ser His
1               5

<210> SEQ ID NO 183
<211> LENGTH: 9
<212> TYPE: PRT
<213> ORGANISM: Leishmania infantum

<400> SEQUENCE: 183

Asn Met Gly Leu Leu Leu Ser Gly Thr
1               5

<210> SEQ ID NO 184
<211> LENGTH: 9
<212> TYPE: PRT
<213> ORGANISM: Leishmania infantum

<400> SEQUENCE: 184

Ser Met Ile Arg Asp Leu Asp Phe Ser
1               5

```
<210> SEQ ID NO 185
<211> LENGTH: 29
<212> TYPE: PRT
<213> ORGANISM: Leishmania infantum

<400> SEQUENCE: 185

Lys Glu Met Pro Ser Gly Ser Asp Tyr Ser His Ser Met Ile Arg Asp
1               5                   10                  15

Leu Asp Phe Ser Asn Met Gly Leu Leu Leu Ser Gly Thr
            20                  25

<210> SEQ ID NO 186
<211> LENGTH: 21
<212> TYPE: PRT
<213> ORGANISM: Leishmania major

<400> SEQUENCE: 186

Thr Asn Thr Leu Ala Val Leu Gln Ala Phe Gly Arg Ala Ile Pro Glu
1               5                   10                  15

Leu Gly Lys Lys Trp
            20

<210> SEQ ID NO 187
<211> LENGTH: 25
<212> TYPE: PRT
<213> ORGANISM: Leishmania major

<400> SEQUENCE: 187

Glu Gly Tyr Phe Val Thr Asp Glu Lys Thr Gly Leu Val Tyr Arg Asp
1               5                   10                  15

Gly Gly Val Ala Ala Ala Ser Ser Gly
            20                  25

<210> SEQ ID NO 188
<211> LENGTH: 19
<212> TYPE: PRT
<213> ORGANISM: Leishmania major

<400> SEQUENCE: 188

Thr Pro Glu Gln Arg Thr Asn Thr Leu Thr Val Glu Leu Gly Lys Lys
1               5                   10                  15

Trp Ile Gly

<210> SEQ ID NO 189
<211> LENGTH: 18
<212> TYPE: PRT
<213> ORGANISM: Leishmania major

<400> SEQUENCE: 189

Thr Leu Pro Glu Met Pro Val Gly Val Pro Glu Met Pro Ala Gly Val
1               5                   10                  15

Asp Tyr

<210> SEQ ID NO 190
<211> LENGTH: 28
<212> TYPE: PRT
<213> ORGANISM: Leishmania major

<400> SEQUENCE: 190

Ala Arg Gly Arg Glu Gly Tyr Phe Leu Ala Arg Gly Ala Arg Gly Arg
1               5                   10                  15
```

```
Glu Gly Tyr Glu Gly Tyr Phe Val Thr Asp Glu Lys
            20                  25
```

MULTI-EPITOPIC PEPTIDE COMPOUNDS AND VACCINES AGAINST LEISHMANIASIS

FIELD OF THE INVENTION

The present invention relates to peptide compounds comprising epitopes, pharmaceutical compositions comprising such peptide compounds, nucleotide sequences coding for the epitopes included in these peptide compounds or for said peptide compounds, expression vectors comprising at least one of these nucleotide sequences, diagnostic reagents comprising said peptide compounds, as well as prophylactic and/or therapeutic vaccines, intended to be used against one or more of the leishmaniases.

PRIOR ART

The cutaneous (CL), mucocutaneous (MCL) and diffuse cutaneous and visceral (VL) forms of leishmaniases are among the most serious parasitic infections affecting humans. They constitute a veritable public health problem, in particular in Latin America, Asia, Africa and southern Europe.

To patients having the symptoms of a leishmaniasis, there are added a large number of asymptomatic individuals who are nevertheless infected but are not treated since they are not diagnosed. The southern Mediterranean region is a zone where *L. infantum* is endemic. In this region, more than 20% of the population of blood donors are infected whereas only a few cases of clinical VL are diagnosed. The ratio of asymptomatic individuals to symptomatic individuals is even higher in zones where *L. donovani* is endemic. This is because, in these zones, this ratio is between approximately 9/1 and approximately 3/1.

Eliminating leishmaniases must take into consideration asymptomatic individuals, who are considered to be potential reservoirs of *Leishmania*.

Although current chemotherapy treatments such as, for example, treatments using AmBisome™, have made considerable progress, a therapeutic approach cannot apply to asymptomatic carriers.

Vaccination is the most suitable means for interrupting the transmission of *Leishmania* parasites and eliminating leishmaniases.

At the present time, canine vaccines are used. Mention will be made for example of the CaniLeish™, Leish-Tec™ or Leishmune™ vaccines. However, no vaccine for human application is available.

Such a human vaccine would however have important health and socioeconomic consequences. In particular coupled to the use of a canine vaccine, use thereof would lead not only to a reduction in the canine reservoir of visceral leishmaniasis, but also to a significant reduction in the most incapacitating or even fatal human pathologies. This is because, in the same way as malaria, leishmaniasis has a great effect on people and the economy, and prophylaxis thereof should significantly improve the socioeconomic context of the most seriously affected countries.

Developing a human vaccine by transposing a canine vaccine such as CaniLeish™ to humans has been imagined, this canine vaccine being the object of the patent document WO 9426899, or using solely one of the major immunogens of the vaccine, the object of the patent document WO 2015/079420, or by using solely peptidic derivatives of this major immunogen, the object of the patent document WO 2014/102471, which discloses in particular the following peptides:

B9 (SEQ ID NO: 186):
T-N-T-L-A-V-L-Q-A-F-G-R-A-I-P-E-L-G-K-K-W

B10 (SEQ ID NO: 187):
E-G-Y-F-V-T-D-E-K-T-G-L-V-Y-R-D-G-G-V-A-A-A-S-S-G

B11 (SEQ ID NO: 188):
T-P-E-Q-R-T-N-T-L-T-V-E-L-G-K-K-W-I-G

B12 (SEQ ID NO: 189):
T-L-P-E-M-P-V-G-V-P-E-M-P-A-G-V-D-Y

B13 (SEQ ID NO: 190):
A-R-G-R-E-G-Y-F-L-A-R-G-A-R-G-R-E-G-Y-E-G-Y-F-V-T-D-E-K.

However, transposing the active principle of this vaccine or of the major immunogen alone to human medicine cannot be envisaged because of the industrial constraints relating in particular to the production of human vaccines, and the costs incurred. The use alone of these peptide derivatives of the major immunogen can also not be envisaged since they have an insufficient degree of vaccine coverage for the populations concerned and too low an in vitro efficacy to stimulate human cells and to produce cytokines of the Th1 type such as IFN-γ, even in 2 µM combinations for each peptide.

Furthermore, other arguments are also in favor of developing a vaccine specific to the prevention of human leishmaniases. This is because it has been shown that curing this illness is generally associated with the development of immunity against reinfection. In cured individuals, a specific cell immune response of the parasitic antigens is observed both in vivo, in the delayed hypersensitivity reaction in response to the skin test for *Leishmania*, and in vitro, when the peripheral-blood mononucleated cells (PBMCs) of these individuals are stimulated, with *Leishmania* antigens.

SUMMARY OF THE INVENTION

Having regard to the above, a technical problem that the invention sets out to solve is developing peptide compounds comprising novel epitopes, pharmaceutical compositions and diagnostic reagents comprising such peptide compounds, having high immunogenic capability against leishmaniases, and allowing the development of effective prophylactic and/or therapeutic vaccines intended to be used effectively against one or more of the *Leishmania* species, which are financially accessible to the populations concerned.

The first object of the solution of the invention to this problem is a peptide compound comprising at least two epitopes contained in the protein sequences chosen from the PSA, H2B or LmLRAB *Leishmania* proteins having a sequence chosen from the sequences SEQ ID NO: 1 to 21, the sequences SEQ ID NO: 24 to 64, the sequences SEQ ID NO: 67, 68, 70 to 72, 74 to 76, the sequences SEQ ID NO: 78 to 95, the sequences SEQ ID NO: 98 to 136, the sequences SEQ ID NO: 139 to 156, and the sequences SEQ ID NO: 158 to 184, as well as the analogous, mutein and homologous derivatives thereof, said epitopes optionally being separated by a peptide spacer comprising at least one amino acid.

The second object thereof is a specific antibody and immunoserum containing same directed against epitopes of the aforementioned peptide compounds.

The third object thereof is a pharmaceutical composition comprising at least one peptide compound as above.

The fourth object thereof is a composition comprising at least one peptide compound as above, for manufacturing a drug or a vaccine, an in vivo or in vitro diagnostic reagent for inducing or diagnosing in mammals an activation of type Th1 lymphocyte-dependent cell-mediated immunity and/or effector humoral immunity.

The fifth object thereof is a prophylactic and/or therapeutic vaccine intended to be used against one or more of the *Leishmania* chosen from *Leishmania donovani, Leishmania infantum, Leishmania chagasi, Leishmania mexicana, Leishmania amazonensis, Leishmania venezuelensis, Leishmania tropica, Leishmania major, Leishmania aethiopica, Leishmania (Viannia) braziliensis, Leishmania (Viannia) guyanensis, Leishmania (Viannia) panamensis,* and/or *Leishmania (Viannia) peruviana*, comprising at least one peptide compound as above.

The sixth object thereof is a nucleotide sequence coding for epitopes included in the above peptide compounds or for said peptide compounds.

The seventh object thereof is an expression vector comprising at least one nucleotide sequence as above, as well as the means necessary for expression thereof.

The eighth object thereof is a diagnostic reagent comprising a peptide compound as above.

Advantageously, the peptide compound is a peptide compound wherein said analogous, mutein and homologous derivatives of the epitopes, having immunogenic capability, have a sequence identity percentage of at least 50%, preferably at least 75% with the sequence of said epitopes; the peptide spacer comprises 1 to 8 amino acids; the peptide compound comprises 2, 3 or 4 of said epitopes; a first epitope is chosen from said epitopes contained in the sequence of a first protein of the proteins chosen from PSA, H2B or LmLRAB, a second epitope is contained in the sequence of a second protein, different from the first protein, and chosen from PSA, H2B or LmLRAB; the peptide compound is a compound wherein the epitopes are chosen from the epitopes of sequence SEQ ID NO: 22, 23, 65, 66, 69, 73, 77, 96, 97, 137, 138, 157 and 185; the peptide compound includes at least three epitopes contained in the sequences of different proteins chosen from PSA, H2B and LmLRAB; the composition comprises at least one peptide compound as above and is intended to be used in prophylactic and therapeutic vaccination directed against *Leishmania*; the *Leishmania* are *Leishmania donovani, Leishmania infantum, Leishmania chagasi, Leishmania mexicana, Leishmania amazonensis, Leishmania venezuelensis, Leishmania tropica, Leishmania major, Leishmania aethiopica, Leishmania (Viannia) braziliensis, Leishmania (Viannia) guyanensis, Leishmania (Viannia) panamensis* and/or *Leishmania (Viannia) peruviana*; the composition comprises at least one peptide compound as above, for manufacturing a drug or a vaccine, or a reagent for in vivo or in vitro diagnosis for inducing or diagnosing in mammals an activation of type Th1 lymphocyte-dependent cell-mediated immunity and/or effector humoral immunity; the vaccine comprises firstly at least one peptide compound chosen from SEQ ID NO: 22, 23, 69, 73 and 77, as well as the analogous, mutein and homologous derivatives thereof; and secondly at least one peptide compound chosen from the sequences SEQ ID NO: 65, 66, 96, 97, 137, 138, 157 and 185, as well as the analogous, mutein and homologous derivatives thereof; the vaccine comprises firstly at least one or two peptide compounds chosen from SEQ ID NO: 22, 23, 69, 73 and 77 as well as the analogous, mutein and homologous derivatives thereof; and secondly at least one, two or three peptide compounds chosen from the sequences SEQ ID No. 65, 66, 96, 97, 137, 138, 157 and 185 as well as the analogous, mutein and homologous derivatives thereof; the vaccine comprises, in combination, the following multiepitope peptide compounds: SEQ ID NO: 23, 66, 73, 77, 97, 138, 157 and 185 as well as the analogous, mutein and homologous derivatives thereof; SEQ ID NO: 23, 66, 157 and 185 as well as the analogous, mutein and homologous derivatives thereof; SEQ ID NO: 66, 97, 138, 157 and 185 as well as the analogous, mutein and homologous derivatives thereof; or SEQ ID NO: 66, 157 and 185 as well as the analogous, mutein and homologous derivatives thereof; and the vaccine further comprises an adjuvant chosen from the adjuvants in classes TLR3, TLR4, TLR5, TLR7, TLR8 and TLR9, saponins and the QA21, quilA or QS21 derivatives thereof, oil in water or water in oil emulsions, polysaccharides, cationic liposomes, virosomes or polyelectrolytes and the immunomodulators chosen from sandfly saliva proteins, cytokines, peptides and heat shock proteins; the vaccine is intended for subcutaneous, intradermal, intramuscular, parenteral, endonasal, mucosal or oral administration.

BRIEF DESCRIPTION OF THE FIGURES

The invention will be better understood from a reading of the following non-limitative description, drawn up with regard to the accompanying drawings, wherein:

Figure 1:
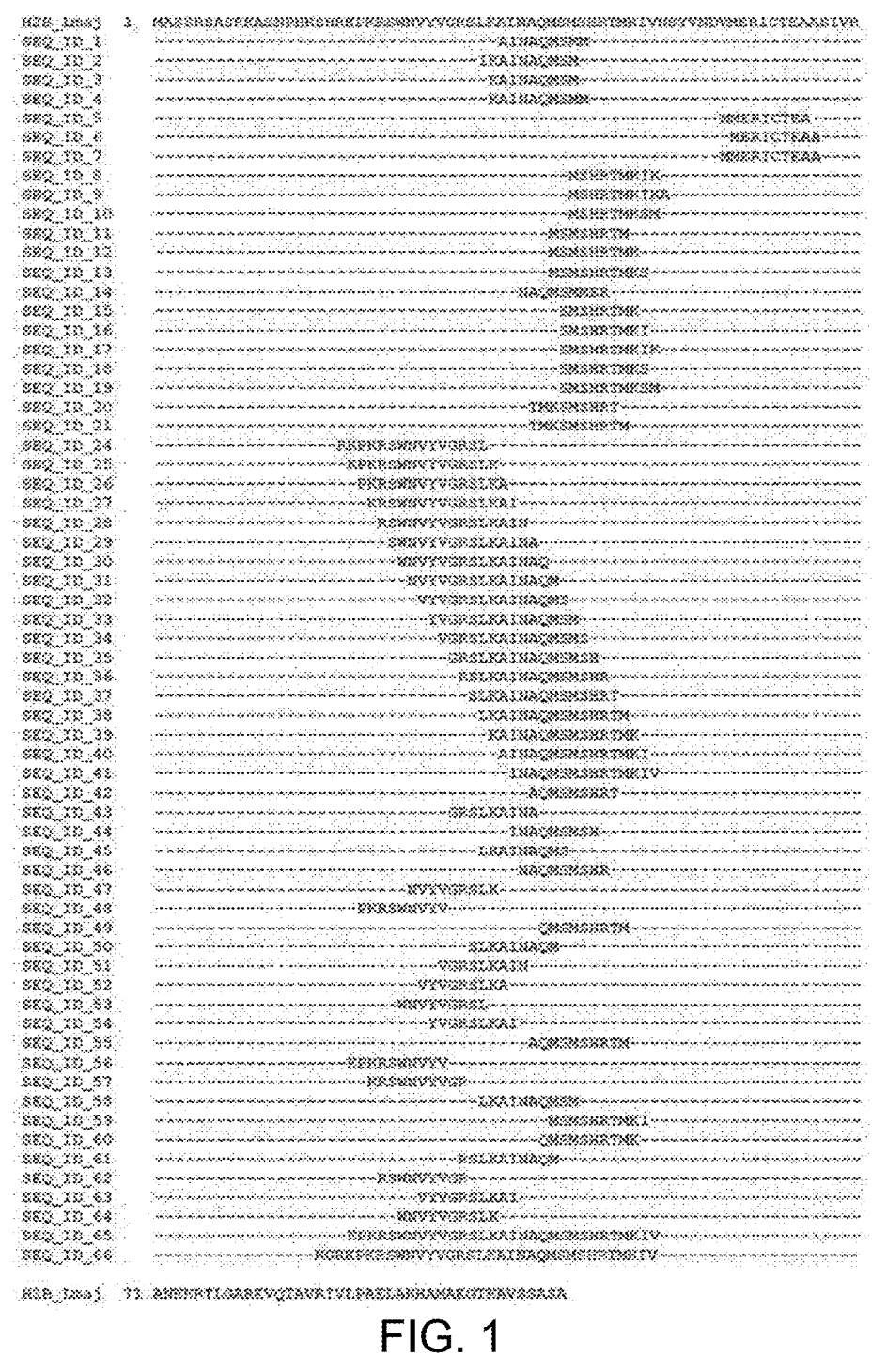

FIG. 1 shows the location of the HLA-I and HLA-II epitopes of sequences SEQ ID NO: 1 to 66 on the sequence of the H2B protein of *L. major* (GenBank accession No AAK21263);

FIGS. 2A, 2B and 2C show the location of the HLA-I epitopes of sequences SEQ ID NO: 67-68, 70-72 and 74-76 (FIG. 2A), the location of the HLA-I and HLA-II epitopes of sequences SEQ ID NO: 78 to 97 (FIG. 2B), and the location of the HLA-I and HLA-II epitopes of sequences SEQ ID NO: 98 to 138 (FIG. 2C) on the sequence of the LmLRAB protein of *L. major* (GenBank accession NO: XP 001685071);

Figure 3B:
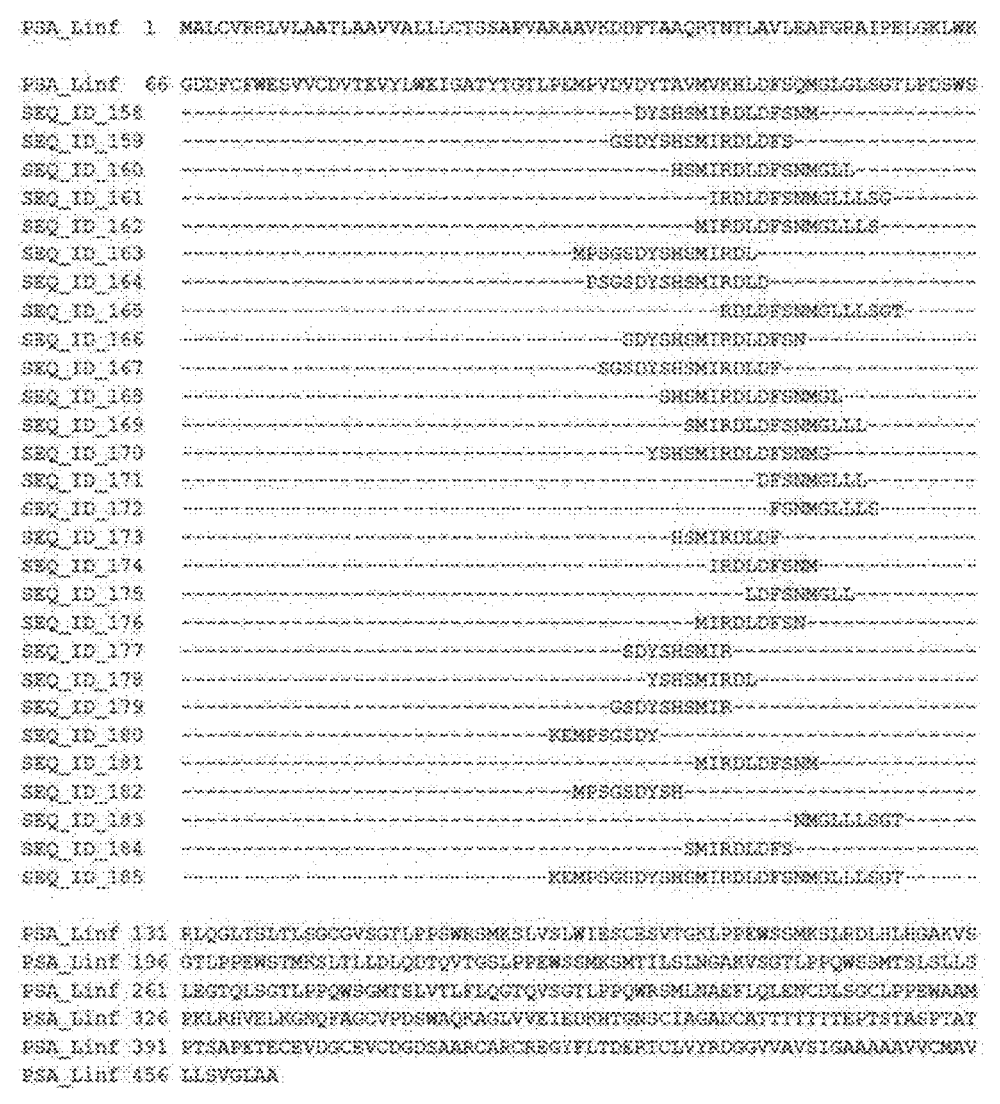

FIGS. 3A and 3B show the location of the HLA-I and HLA-II epitopes of sequences SEQ ID NO: 139 to 157 (FIG. 3A) and the location of the HLA-I and HLA-II epitopes of sequences SEQ ID NO: 158 to 185 on the sequence of the PSA protein of *L. infantum* (GenBank accession No ACY70941) (FIG. 3B);

FIG. 4 is a table that shows the levels of IFN-γ secreted by the PBMCs (peripheral blood mononuclear cells) of individuals cured of cutaneous leishmaniasis and stimulated in vitro by peptide compounds of the present invention according to a short 10-day protocol with a stimulation at D0 and addition of recombinant IL-2 at D1, D4 and D7. The levels of IFN-γ may reach more than 2700 pg/ml with a combination of the peptide compounds according to the invention, which shows a very high added value of these peptides according to the invention. The compounds used in these mixtures were obtained by chemical synthesis with addition of a palmitoylated tail at the amino-terminal end and without modification of the carboxy-terminal end;

DETAILED DESCRIPTION OF THE INVENTION

According to the invention, "epitope" means a peptide compound or a peptide defined by the sequence thereof having approximately 8 to 15 amino acids.

According to the invention, "analogous derivatives" or "mutein derivatives" of a peptide compound means the biologically active derivatives of the reference molecules that have the required activity, namely the ability to stimulate a cell-mediated immune response. In general, the term "analogous derivatives" refers to compounds having a sequence and a polypeptide structure having one or more additions, substitutions and/or deletions of amino acids, with respect to the peptide compounds defined above, insofar as these modifications do not destroy the immunogenic activity. According to the invention, the "analogs" particularly preferred include the preserving substitutions, that is to say the substitutions or replacements without any consequences on the function and the final structure of the protein. The term "mutein derivative" means the peptides having one or more elements imitating the peptide. Methods for preparing conventional analogs and muteins are known to persons skilled in the art.

According to the invention, "homologous derivatives" means peptide compounds having a certain percentage of peptide identify. The term "identity" signifies that the amino acids of two peptide sequences compared correspond exactly. The percentage of identity is determined by a direct comparison of the sequences between two peptide compounds by aligning said sequences and counting the exact number of mismatches between the two aligned sequences. Next, a division by the length of the shortest sequence is carried out and the result is multiplied by a hundred. The percentage identity can also be determined by means of computer programs well known to persons skilled in the art. Thus, according to the invention, two peptide sequences are said to be "substantially homologous" with respect to each other provided that they have at least 50%, preferably at least 70%, preferably again at least 75%, preferably again at least 85%, preferably again at least 90% and even more preferably at least 95% or more identity of sequence over a defined length of the peptide molecules.

The vaccine strategy according to the invention is intended to respond to the need for a vaccine providing good coverage of the worldwide human population and protecting against the main species of leishmaniasis. It is based on fragments of antigenic peptides capable of lastingly activating specific cell immunity directed against these parasites. Peptide vaccination is based on the molecular and cellular bases of the recognition of the antigen by the T cells. The establishment of specific immunity depends, to a large extent, on the degradation and the association of the antigenic fragments, peptides, with the molecules of the major histocompatibility complex (MHC; HLA for humans). This association is made specific of a particular HLA molecule by amino acid residues constituting the anchor units of the peptide. The complexes thus formed are recognized by the T lymphocytes by means of a membrane receptor (TcR) and requires a specific interaction with certain amino acids of the T epitope. The T epitopes are ligands of the HLA molecules with strong or moderate affinities. They are presented to the CD8+ (cytotoxic) or CD4+ (auxiliary) T lymphocytes by the HLA molecules respectively of class I or class II. The formation of these tri-molecular complexes (TcR/HLA/peptide) is the prerequisite for the activation and the expansion of the specific T cells and therefore for the induction of a protective immune response during an infection.

The vaccine strategy according to the invention relies on the identification and selection of immunodominant peptides carried by the sequences of the following specific proteins of *Leishmania*:
  i) a virulence protein characterized as the major immunogen of the antigens excreted/secreted by *Leishmania*, namely the soluble PSA protein, which is common and very much preserved within the species of *leishmania*, responsible for the various human infections;
  ii) an H2B protein, which is highly preserved among the species of *Leishmania*, which is capable of inducing protection in the murine model and a cell response in humans, and the N-terminal region of which, which is the most divergent with respect to the histone proteins of mammals, is capable of conferring significant protection against a challenge with virulent parasites in BALB/c mice. The H2B protein is recognized by T lymphocytes of individuals cured of *L. tropica* or *L. major*, with an induction of high levels of IFN-γ; and
  iii) an LmLRAB protein, belonging to the superfamily of RAB GTPases, and highly preserved with other species of *Leishmania*, capable of inducing significantly high levels of IFN-γ in individuals cured of cutaneous leishmaniasis.

The advantage of such peptides is multiple:
  (i) they have high innocuity since they avoid any infectious risk related to the use of a pathogenic agent or infectious agent;
  (ii) they are chemically well defined and thus meet the pharmaceutical requirements for purity;
  (iii) they facilitate monitoring of the induced immune response (search for cytotoxic T lymphocytes (CTLs) directed against a defined T epitope); and
  (iv) their sequence can be modified in order to make them more immunogenic.

Such peptides meet in a remarkable fashion all the conditions mentioned in the preamble of the present application: reproducible vaccine, thermostable facilitating storage and transport thereof, multipurpose, easy to produce at low cost in the endemic zones, making it possible to use it on a large scale.

Advantageously, the epitopes or peptide compounds that are the object of the invention are linked to carriers for making them more immunogenic. By way of non-limitative examples of carriers, mention can be made of the KLM (keyhole limpet hemocyanin) carrier proteins, and the lipopeptides of the palmitoyl type, or derivatives thereof. The most usual modifications to proteins by lipids are: isoprenylation, N-myristoylation, palmitoylation (or S-acylation) and glypiation. Isoprenylation and N-myristoylation are co-translational or immediately post-translational modifications and the group that is attached remains so until the protein degrades. Palmitoylation is post-translational. This modification is reversible and quicker than the turnover or degradation of the proteins:

it can therefore be regulated. Glypiation is co- and post-translational. Palmitoylated peptides are particularly advantageous according to the invention since these derivatives interact with the lipidic components of the membrane of the target cells (macrophages, dendritic cells, neutrophils, etc.), assist penetration thereof and convey them inside them in order then to present them to the immune system.

The epitopes according to the invention furthermore advantageously have one or more protective groups. This is because, so as to improve resistance to degradation, it may be opportune to use a protected form of the peptide according to the invention. The protection form is a biologically compatible form and is compatible with use in the pharmaceutical field. Numerous forms of biologically compatible protection can be envisaged, such as for example acylation or acetylation of the amino-terminal end, or amidation or esterification of the carboxy-terminal end, as is the case, for example, with compounds obtained by chemical synthesis with the addition of a palmitoylated tail at the amino-terminal end and amidation of the carboxy-terminal end, with levels of IFN-γ secreted by the PBMCs of individuals cured of cutaneous leishmaniasis and stimulated in vitro by mixtures of peptide compounds of the present invention in accordance with a short 10-day protocol with stimulation at D0 and addition of recombinant IL-2 at D1, D4 and D7. The levels of IFN-γ obtained with a combination of the peptide compounds according to the invention also shows a high added value of the compounds according to the invention. Thus the invention also relates to an epitope as defined previously, characterized by the fact that it is in protected form. It is possible to use a protection based on a substitution on the amino-terminal end by an acetyl group, a benzoyl group, a tosyl group or a benzyloxycarbonyl group. Preferably, use is made of a protection based on the amidation of the hydroxyl function of the carboxy-terminal end by an NYY group with Y representing a C1 to C4 alkyl chain, or esterification by an alkyl group. It is possible to protect both ends of the peptide compound.

The peptide derivatives according to the invention also relate to the amino acids and peptides linked together by a pseudopeptide bond. Pseudopeptide bond means all the types of bond able to replace conventional peptide bonds. In the field of amino acids, the geometry of the molecules is such that they can theoretically be in the form of different optical isomers. There exists, in fact, a molecular conformation of amino acid (aa) such that it diverts to the right the polarization plane of light (dextrorotatory or D-aa conformation), and a molecular conformation of the amino acid (aa) such that it diverts to the left the polarization plane of light (levogyre or L-aa conformation). Natural amino acids are always of levogyre conformation, and consequently a peptide of natural origin will consist only of amino acids of the L-aa type. However, chemical synthesis in the laboratory makes it possible to prepare amino acids having both possible conformations.

From this basic material, it is thus possible, when synthesizing a peptide, to incorporate amino acids in the form of both dextrorotatory or levogyre optical isomers. Thus the amino acids constituting the peptide according to the invention may be in L-, D- or DL-configuration.

The epitopes and peptide compounds according to the invention can be obtained either by conventional chemical synthesis in solid phase or in liquid homogeneous phase, or by enzymatic synthesis, from constituent amino acids or derivatives thereof. The epitopes and peptide compounds according to the invention can also be obtained by fermentation of a strain of bacteria, modified or not, by genetic engineering, or by extraction of proteins of animal or vegetable origin, preferably of vegetable origin, followed by a controlled hydrolysis that releases peptidic fragments corresponding totally or partially to the epitopes and peptide compounds according to the invention.

The Applicant has been able to show that the various epitopes according to the invention are consensus sequences common to the main species of *Leishmania* and have a strong or moderate affinity for all the molecules of the MHC (major histocompatibility complex) of mammals, and more particular for all the molecules of the HLAs (HLAs standing for human leucocyte antigens), mainly represented by the human populations most seriously affected by these ailments.

This is because, in the context of a strategy of vaccination of human populations exposed to *Leishmania* infections and in order to meet the need for a vaccine providing good coverage of the world population and protecting against leishmaniases, it is important to use antigen/peptide fragments capable of activating, lastingly, specific cell immunity directed against the parasite.

In order to ensure good coverage of the world population and having regard to the great variability of the HLA phenotype (the major human histocompatibility complex) between individuals, the immunogenic antigen fragments (peptides) of sufficient length must contain a series of epitopes able to be presented by several types of HLA molecules of class I and II.

HLA molecules are highly polymorphous. This is because there exist more than 2500 HLA proteins of class I (HLA-I) and more than 1000 HLA proteins of class II (HLA-II). However, some of these HLA molecules, close in sequence and in spatial conformation, may have epitopes common to the T cells. The grouping of several thousands of HLA molecules is at the present time described in a little more than 20 or so categories, referred to as "HLA supertypes" having epitopes that are very well preserved for each supertype.

To the development of peptide vaccines, there is added the multiepitope or polyepitope approach (a peptide containing a plurality of epitopes). This multiepitope approach is advantageous for developing a vaccine intended for the whole of the world population. This is because, in order to ensure good coverage of the world population and having regard to the great variability of the HLA phenotype between individuals, immunogenic antigen fragments (peptides) of sufficient length must contain a series of epitopes able to be presented by several supertypes of HLA-I and -II molecules.

Thus the epitopes included in the peptide compounds of the invention have great immunogenic capacity.

T epitopes are antigen sequences that recognize T lymphocytes. For example, in humans, T epitopes result from the degradation of antigens by the presenting cells and are presented to the CD8+ (cytotoxic) or CD4+ (auxiliary) T lymphocytes by the HLA molecules respectively of class I or class II. T epitopes are therefore necessarily ligands of HLA molecules and effectively form part of the peptides, which bind to the HLA molecules with strong and moderate affinities.

The cells expressing the major histocompatibility complex of class II (CMH2) may also present microbial antigens via CD1 to gamma-delta T lymphocytes.

The presentation capabilities depend on numerous variables. They vary from one individual to another because of the polymorphism of the major histocompatibility complex (MHC).

Thus consanguinity, by reducing the number of different MHCs expressed by an individual, reduces their immune capacities. They also differ according to the ways of exposure to the antigen (dose and administration route), because of the variations in the presentation capacities of the various types of presenting cells. For example, the cells involved in the presentation will be different by cutaneous or digestive route.

Finally, the peptide range produced by a given antigen will be different according to the presenting cell (cleavage methods), and according to the species and the individual (the allele of the MHC).

The peptide compounds according to the invention have been selected and designed so as to ensure vaccinal and therapeutic coverage of the populations most seriously affected by the main pathogenic species of *Leishmania*. They are intended to induce and to characterize the prevention or treatment of ailments in mammals the protective immunity of which depends on the stimulation of the type Th1 leucocytes and cytotoxic T cells, characteristic of a state of hyperstimulation of a delayed type.

As is described above, another main difficulty in the development of a vaccine candidate lies in the fact that it must ideally be effective against several species of *Leishmania* and in particular against the most severe clinical forms (visceral and cutaneous) and in various natural hosts of the infection (humans, dogs).

The sequences of these epitopes are preferentially:
the peptide sequence of H2B proteins contained in Table 1 below;
the peptide sequences of LmLRAB proteins contained in Table 2 below;
the peptide sequences of PSA proteins contained in Table 3 below,
as well as the analogous, mutein and homologous derivatives thereof.

TABLE 1

| | | | | |
|---|---|---|---|---|
| | | H2B | | |
| SEQ ID H2B-1 | Peptide | Affinity for the HLA alleles of class I | Affinity for the HLA supertypes of class I | Affinity for the HLA alleles of class II |
| SEQ ID NO: 1 | AINAQMSMM | HLA-B*15:01 | HLA-B*62 | |
| SEQ ID NO: 2 | IKAINAQMSM | HLA-B*15:01, HLA-B*57:01 | HLA-B*58, HLA-B*62 | |
| SEQ ID NO: 3 | KAINAQMSM | HLA-B*58:01, HLA-B*57:01, HLA-B*15:01, HLA-A*30:01 | HLA-A*01/HLA-A*03, HLA-B*58, HLA-B*62 | HLA-DRB4*01:01 |
| SEQ ID NO: 4 | KAINAQMSMM | HLA-B*58:01, HLA-B*57:01, HLA-B*15:01 | HLA-B*58, HLA-B*62 | |
| SEQ ID NO: 6 | MERICTEAA | HLA-B*40:02, HLA-B*45 | HLA-B*44:01 | |
| SEQ ID NO: 5 | MMERICTEA | HLA-A*02:03, HLA-A*02:01 | HLA-A*02 | |
| SEQ ID NO: 7 | MMERICTEAA | HLA-A*02:03 | HLA-A*02 | |
| SEQ ID NO: 8 | MSHRTMKIK | HLA-A*30:01, HLA-A*03:01, HLA-A*11:01 | HLA-A*01/HLA-A*03, HLA-A*03 | |
| SEQ ID NO: 9 | MSHRTMKIKA | HLA-A*30:01 | HLA-A*01/HLA-A*03 | |
| SEQ ID NO: 10 | MSHRTMKSM | HLA-B*57:01, HLA-A*30:01, HLA-B*15:01, HLA-B*62 | HLA-A*01/HLA-A*03, HLA-B*58, | |
| SEQ ID NO: 11 | MSMSHRTM | HLA-B*08:01 | HLA-B*08 | |
| SEQ ID NO: 12 | MSMSHRTMK | HLA-A*11:01, HLA-A*31:01, HLA-A*03:01, HLA-A*68:01, HLA-A*30:01, HLA-A*33:01 | HLA-A*01/HLA-A*03, HLA-A*03 | HLA-DRB1*03:01, HLA-DRB1*09:01, HLA-DRB1*11:01 |
| SEQ ID NO: 13 | MSMSHRTMKS | HLA-A*03:01, HLA-A*11:01 | HLA-A*03 | |
| SEQ ID NO: 14 | NAQMSMMER | HLA-A*68:01, HLA-A*33:01, HLA-A*31:01 | HLA-A*03 | |
| SEQ ID NO: 15 | SMSHRTMK | HLA-A*03:01 | HLA-A*03 | |
| SEQ ID NO: 16 | SMSHRTMKI | HLA-A*02:03, HLA-A*32:01, HLA-A*02:01 | HLA-A*02 | HLA-DRB1*07:01, HLA-DRB1*13:02 |
| SEQ ID NO: 17 | SMSHRTMKIK | HLA-A*03:01, HLA-A*11:01, HLA-A*30:01 | HLA-A*01/HLA-A*03, HLA-A*03 | |
| SEQ ID NO: 18 | SMSHRTMKS | HLA-A*02:03 | HLA-A*02 | |
| SEQ ID NO: 19 | SMSHRTMKSM | HLA-B*15:01, HLA-B*57:01, HLA-A*02:03, HLA-B*08:01 | HLA-A*02, B*08, HLA-B*62 | HLA-B*58, |
| SEQ ID NO: 20 | TMKSMSHRT | HLA-A*02:03 | HLA-A*02 | |
| SEQ ID NO: 21 | TMKSMSHRTM | HLA-B*15:01, HLA-B*08:01 | HLA-B*08, B*62 | HLA- |
| SEQ ID NO: 22 | MSMSHRTMKSMSHRTMKIKAINAQMSMMERICTEAA | | | |
| SEQ ID NO: 23 | KARYMSMSHRTMKSMSHRTMKIKAINAQMSMMERICTEAA | | | |
| SEQ ID H2B-II | Peptide | Concatenation affinity for the HLA alleles of class II | | |
| SEQ ID NO: 24 | RKPKRSWNVYVGRSL | HLA-DRB1*13:02, HLA-DRB1*01:01, HLA-DRB1*07:01, HLA-DRB1*09:01, HLA-DRB1*15:01 | | |
| SEQ ID NO: 25 | KPKRSWNVYVGRSLK | HLA-DRB5*01:01, HLA-DRB1*01:01, HLA-DRB1*07:01, HLA-DRB1*09:01, HLA-DRB1*15:01 | | |

TABLE 1-continued

| | H2B | |
|---|---|---|
| SEQ ID NO: 26 | PKRSWNVYVGRSLKA | HLA-DRB5*01:01, HLA-DRB1*01:01, HLA-DRB1*11:01, HLA-DRB5*13:02, HLA-DRB5*07:01, HLA-DRB5*09:01, HLA-DRB5*15:01 |
| SEQ ID NO: 27 | KRSWNVYVGRSLKAI | HLA-DRB1*01:01, HLA-DRB1*03:01, HLA-DRB1*04:01, HLA-DRB1*11:01, HLA-DRB1*13:02, HLA-DRB1*07:01, HLA-DRB1*09:01, HLA-DRB1*15:01, HLA-DRB5*01:01, HLA-DPA1*02:01/DPB1*01:01 |
| SEQ ID NO: 28 | RSWNVYVGRSLKAIN | HLA-DRB5*01:01, HLA-DRB1*01:01, HLA-DRB1*03:01, HLA-DRB1*04:01, HLA-DRB1*11:01, HLA-DRB1*13:02, HLA-DRB1*04:05, HLA-DRB1*07:01, HLA-DRB1*09:01, HLA-DRB1*15:01, HLA-DPA1*02:01/DPB1*01:01, HLA-DRB1*08:02 |
| SEQ ID NO: 29 | SWNVYVGRSLKAINA | HLA-DRB5*01:01, HLA-DRB1*04:05, HLA-DPA1*03:01/DPB1*04:02, HLA-DRB1*01:01, HLA-DRB1*03:01, HLA-DRB1*04:01, HLA-DRB1*11:01, HLA-DRB1*13:02, HLA-DRB1*07:01, HLA-DRB1*09:01, HLA-DRB1*15:01, HLA-DPA1*02:01/DPB1*01:01, HLA-DRB1*08:02 |
| SEQ ID NO: 30 | WNVYVGRSLKAINAQ | HLA-DRB5*01:01, HLA-DRB1*04:05, HLA-DPA1*03:01/DPB1*04:02, HLA-DRB1*01:01, HLA-DRB1*03:01, HLA-DRB1*04:01, HLA-DRB1*11:01, HLA-DRB1*07:01, HLA-DRB9*01:01, HLA-DRB1*15:01, HLA-DPA1*02:01/DPB1*01:01, HLA-DRB1*08:02 |
| SEQ ID NO: 31 | NVYVGRSLKAINAQM | HLA-DRB1*04:01, HLA-DRB4*01:01, HLA-DRB1*03:01, HLA-DRB1*04:05, HLA-DRB1*11:01, HLA-DRB1*01:01, HLA-DRB1*09:01, HLA-DRB1*15:01, HLA-DRB1*08:02 |
| SEQ ID NO: 32 | VYVGRSLKAINAQMS | HLA-DRB1*01:01, HLA-DRB1*04:05, HLA-DRB1*07:01, HLA-DRB4*01:01, HLA-DRB1*04:01, HLA-DRB1*09:01, HLA-DRB1*03:01, HLA-DRB1*11:01, HLA-DRB1*15:01, HLA-DRB1*08:02 |
| SEQ ID NO: 33 | YVGRSLKAINAQMSM | HLA-DRB1*01:01, HLA-DRB1*04:05, HLA-DRB1*07:01, HLA-DRB1*09:01, HLA-DRB4*01:01, HLA-DRB5*01:01, HLA-DRB1*04:01, HLA-DRB1*11:01, HLA-DRB1*08:02, |
| SEQ ID NO: 34 | VGRSLKAINAWMSMS | HLA-DRB1*01:01, HLA-DRB1*04:05, HLA-DRB1*07:01, HLA-DRB1*09:01, HLA-DRB4*01:01, HLA-DRB5*01:01, HLA-DRB1*04:01, HLA-DRB1*08:02, HLA-DRB1*11:01, HLA-DRB1*13:02 |
| SEQ ID NO: 35 | GRSLKAINAQMSMSH | HLA-DRB1*15:01, HLA-DRB1*01:01, HLA-DRB1*04:05, HLA-DRB1*07:01, HLA-DRB1*08:02, HLA-DRB1*09:01, HLA-DRB1*11:01, HLA-DRB4*01:01, HLA-DRB5*01:01, HLA-DRB1*04:01, HLA-DRB1*13:02 |
| SEQ ID NO: 36 | RSLKAINAWMSMSHR | HLA-DRB1*04:01, HLA-DRB1*15:01, HLA-DRB1*05:01, HLA-DRB1*01:01, HLA-DRB1*04:05, HLA-DRB1*07:01, HLA-DRB1*08:02, HLA-DRB1*09:01, HLA-DRB1*11:01, HLA-DRB4*01:01, |
| SEQ ID NO: 37 | SLKAINAQMSMSHRT | HLA-DRB1*07:01, HLA-DRB1*04:01, HLA-DRB1*04:05, HLA-DRB1*09:01, HLA-DRB1*11:01, HLA-DRB1*15:01, HLA-DRB5*01:01, HLA-DRB1*01:01, HLA-DRB1*08:02, HLA-DRB4*01:01, |
| SEQ ID NO: 38 | LKAINAQMSMSHRTM | HLA-DRB1*07:01, HLA-DRB1*04:01, HLA-DRB1*04:05, HLA-DRB1*09:01, HLA-DRB1*11:01, HLA-DRB1*15:01, HLA-DRB5*01:01, HLA-DRB1*01:01, HLA-DRB4*01:01, |
| SEQ ID NO: 39 | KAINAQMSMSHRTMK | HLA-DRB1*07:01, HLA-DRB1*04:01, HLA-DRB1*04:05, HLA-DRB1*09:01, HLA-DRB1*11:01, HLA-DRB1*15:01, HLA-DRB5*01:01, HLA-DRB4*01:01, HLA-DRB1*03:01, HLA-DRB1*01:01 |
| SEQ ID NO: 40 | AINAQMSMSHRTMKI | HLA-DRB1*01:01, HLA-DRB1*04:01, HLA-DRB1*09:01, HLA-DRB1*15:01, HLA-DRB4*01:01, HLA-DRB5*01:01, HLA-DRB3*01:01, HLA-DRB1*11:01, HLA-DRB1*07:01 |
| SEQ ID NO: 41 | INAQMSMSHRTMKIV | HLA-DRB1*04:01, HLA-DRB1*15:01, HLA-DRB1*05:01, HLA-DRB1*03:01, HLA-DRB1*09:01, HLA-DRB1*11:01, HLA-DRB1*01:01, HLA-DRB4*01:01, HLA-DRB1*07:01, HLA-DRB1*13:02 |

| | Peptide-core epitope | Affinity HLA alleles of class II | Affinity HLA alleles of class I | Affinity HLA supertype allele of class I |
|---|---|---|---|---|
| SEQ ID NO: 42 | AQMSMSHRT | HLA-DRB1*01:01, HLA-DRB1*07:01 | | |
| SEQ ID NO: 43 | GRSLKAINA | HLA-DRB1*01:01 | | |
| SEQ ID NO: 44 | INAQMSMSH | HLA-DRB1*04:01, HLA-DRB1*04:05, HLA-DRB1*09:01, HLA-DRB1*11:01, HLA-DRB1*15:01, HLA-DRB4*01:01, HLA-DRB5*01:01 | | |

TABLE 1-continued

H2B

| SEQ ID NO: | Epitope | | | |
|---|---|---|---|---|
| SEQ ID NO: 45 | LKAINAQMS | HLA-DRB1*01:01, HLA-DRB1*04:05, HLA-DRB1*07:01, HLA-DRB1*08:02, HLA-DRB1*09:01, HLA-DRB1*11:01, HLA-DRB4*01:01, HLA-DRB5*01:01 | | |
| SEQ ID NO: 46 | NAQMSMSHR | HLA-DRB1*01:01 | | |
| SEQ ID NO: 47 | NVYVGRSLK | HLA-DRB5*01:01 | HLA-A*03:01 | HLA-A*03 |
| SEQ ID NO: 48 | PKRSWNVYV | HLA-DRB1*13:02, HLA-DRB1*15:01 | | |
| SEQ ID NO: 49 | QMSMSHRTM | HLA-DRB1*01:01, HLA-DRB4*01:01 | HLA-B*15:01 | HLA-B*62 |
| SEQ ID NO: 50 | SLKAINAQM | HLA-DRB1*04:01, HLA-DRB1*08:02, HLA-DRB1*09:01, HLA-DRB1*11:01, HLA-DRB1*13:02, HLA-DRB1*04:01 | HLA-B*15:01 | HLA-B*62 |
| SEQ ID NO: 51 | VGRSLKAIN | HLA-DRB1*03:01, HLA-DRB1*04:05, HLA-DRB1*08:02, HLA-DRB1*11:01 | | |
| SEQ ID NO: 52 | VYVGRSLKA | HLA-DRB1*01:01, HLA-DRB1*01:01, HLA-DRB1*03:01, HLA-DRB1*04:01, HLA-DRB1*09:01, HLA-DRB1*11:01, HLA-DRB1*13:02, HLA-DRB1*15:01, HLA-DPA1*03:01/ DPB1*04:02 | | |
| SEQ ID NO: 53 | WNVYVGRSL | HLA-DRB1*01:01, HLA-DRB1*04:05, HLA-DRB1*07:01, HLA-DRB1*09:01, HLA-DRB1*15:01, HLA-DRB5*01:01 | | |
| SEQ ID NO: 54 | YVGRSLKAI | HLA-DRB1*08:02, HLA-DPA1*02:01/ DPB1*01:01 | | |

TABLE 2

LmLRAB

| LmLRAB (IA, IB, IC) SEQ ID | Epitope | Concatenation affinity for HLA allele of class I | Affinity for HLA supertypes of class II |
|---|---|---|---|
| SEQ ID NO: 67 | NENNITGGL | HLA-B*18:01, HLA-B*40:01, HLA-B*40:02, HLA-B*44:02, HLA-B*44:03 | HLA-B*44 |
| SEQ ID NO: 68 | KTKQHLREM | HLA-A*30:01, HLA-A*2602 | HLA-A*01/HLA-A*03, HLA-A*01 |
| SEQ ID NO: 69 | KARYMENNITGGLARYKTKQHVREM (long peptide) | | |
| SEQ ID NO: 70 | RFAQGEHDI | HLA-A*2403 | HLA-A*24 |
| SEQ ID NO: 71 | RLPENAFVI | HLA-A*32:01, HLA-A*02:06, HLA-A*02:11, HLA-A*02:12, HLA-A*02:16, HLA-A*02:19 | HLA-A*01, HLA-A*02 |
| SEQ ID NO: 72 | TQGSSKAGF | HLA-B*15:01, HLA-B*15:02 | HLA-B*27, HLA-B*62 |
| SEQ ID NO: 73 | KARYRFAQGEHDIRLPENAFVIARYTQGSSKAGF (long peptide) | | |
| SEQ ID NO: 74 | MPHVDQSSI | HLA-B*07:02, HLA-B*35:01, HLA-B*51:01, HLA-B*53:01, HLA-B*08:01 | HLA-B*07, HLA-B*08 |

TABLE 2-continued

| | | LmLRAB | |
|---|---|---|---|
| SEQ ID NO: 75 | ASFRSTEAI | HLA-A*32:01, HLA-B*15:03, HLA-B*1517 | HLA-A*01, HLA-B*27, HLA-B*58 |
| SEQ ID NO: 76 | SSIMVVANK | HLA-A*30:01, HLA-A*03:01, HLA-A*11:01, HLA-A*31:01, HLA-A*68:01 | HLA-A*01/HLA-A*03, HLA-A*01 |
| SEQ ID NO: 77 | KARYMPHVDQSSIARYASFRSTEAIRYSSIMVVANK (long peptide) | | |

| LmLRAB-IIA SEQ ID | peptide | Concatenation affinity for HLA alleles of class II |
|---|---|---|
| SEQ ID NO: 78 | KGRLHSVVGRHLSIV | HLA-DRB1*07:01, HLA-DRB5*01:01, HLA-DRB1*11:01, HLA-DRB1*15:01, HLA-DRB1*09:01, HLA-DRB1*01:01, HLA-DRB4*01:01 |
| SEQ ID NO: 79 | GRLHSVVGRHLSIVA | HLA-DRB1*07:01, HLA-DRB5*01:01, HLA-DRB1*15:01, HLA-DRB1*11:01, HLA-DRB1*09:01, HLA-DRB1*01:01, HLA-DRB4*01:01 |
| SEQ ID NO: 80 | RLHSVVGRHLSIVAD | HLA-DRB1*07:01, HLA-DRB1*15:01, HLA-DRB5*01:01, HLA-DRB1*11:01, HLA-DRB1*09:01, HLA-DRB1*01:01 |
| SEQ ID NO: 81 | LHSVVGRHLSIVADH | HLA-DRB1*07:01, HLA-DRB1*15:01, HLA-DRB5*01:01, HLA-DRB1*11:01, HLA-DRB1*09:01, HLA-DRB1*01:01 |
| SEQ ID NO: 82 | HSVVGRHLSIVADHM | HLA-DRB1*01:01, HLA-DRB1*15:01 |
| SEQ ID NO: 83 | SVVGRHLSIVADHMP | HLA-DRB1*01:01, HLA-DRB1*15:01 |
| SEQ ID NO: 84 | VVGRHLSIVADHMPH | HLA-DRB1*01:01 |
| SEQ ID NO: 85 | VGRHLSIVADHMPHL | HLA-DRB1*03:01, HLA-DRB3*01:01, HLA-DRB1*13:02, HLA-DRB1*15:01, HLA-DRB1*01:01 |
| SEQ ID NO: 86 | GRHLSIVADHMPHLD | HLA-DRB3*01:01, HLA-DRB1*03:01, HLA-DRB1*13:02, HLA-DRB1*01:01 |
| SEQ ID NO: 87 | RHLSIVADHMPLHDQ | HLA-DRB3*01:01, HLA-DRB1*03:01, HLA-DRB1*13:02 |

| | Core | Concatenation affinity for HLA alleles of class II | Affinity for HLA alleles of class I |
|---|---|---|---|
| SEQ ID NO: 88 | HLSIVADHM | HLA-DRB1*01:01 | |
| SEQ ID NO: 89 | IVADHMPHL | HLA-DRB1*03:01, HLA-DRB1*13:02, HLA-DRB3*01:01 | HLA-A*02:01, HLA-A*02:03, HLA-A*02:06 |
| SEQ ID NO: 90 | LHSVVGRHL | HLA-DRB1*01:01 HLA-DRB1*07:01 HLA-DRB1*09:01 HLA-DRB1*11:01 HLA-DRB1*15:01 HLA-DRB4*01:01 HLA-DRB5*01:01 | |
| SEQ ID NO: 91 | VGRHLSIVA | HLA-DRB1*01:01, HLA-DRB1*15:01 | |

TABLE 2-continued

LmLRAB

| | Peptide | Affinity allele class I |
|---|---|---|
| SEQ ID NO: 92 | KGRLHSVVG | HLA-A*30:1 |
| SEQ ID NO: 93 | RLHSVVGRH | HLA-A*03:01, HLA-A*30:02 |
| SEQ ID NO: 94 | SVVGRHLSI | HLA-A*02:03, HLA-A*02:06, HLA-A*32:01, HLA-B*08:01 |
| SEQ ID NO: 95 | VVGRHLSIV | HLA-A*02:03 |

Long peptide SEQ ID

| SEQ ID NO: 96 | LHSVVGRHLSIVADHMPHLDQ |
|---|---|
| SEQ ID NO: 97 | KGRLHSVVGRHLSIVADHMPHLDQ |

| LmlRAB-IIB SEQ ID | Peptide | Concatenation affinity for HLA alleles of class II |
|---|---|---|
| SEQ ID NO: 98 | AIVTSRKVQEEVFDL | HLA-DRB1*03:01, HLA-DRB1*11:01, HLA-DRB1*12:01 |
| SEQ ID NO: 99 | DLFTDVHYSEVSAKT | HLA-DRB1*04:01, HLA-DRB7*01:01, HLA-DPA1*01:03/DPB1*02:01, HLA-DPA1*02:01/DPB1*01:01, HLA-DPA1*01/DPB1*04:01, HLA-DPA1*02:01/HLA-DPB1*14:01 |
| SEQ ID NO: 100 | EEVFDLFTDVHYSEV | HLA-DRB1*01:01, HLA-DRB1*03:01, HLA-DRB1*04:01, HLA-DRB1*04:05, HLA-DRB1*07:01, HLA-DRB1*15:01, HLA-DRB1*12:01, HLA-DRB3*01:01, HLA-DPA1*01:03/DPB1*02:01, HLA-DPA1*02:01/DPB1*01:01, HLA-DPA1*01/DPB1*04:01, HLA-DPA1*02:01/HLA-DPB1*14:01 |
| SEQ ID NO: 101 | ENAIVTSRKVQEEVF | HLA-DRB1*03:01, HLA-DRB1*07:01, HLA-DRB1*08:02, HLA-DRB1*11:01, HLA-DRB1*12:01 |
| SEQ ID NO: 102 | EVFDLFTDVHYSEVS | HLA-DRB1*01:01, HLA-DRB1*03:01, HLA-DRB1*04:01, HLA-DRB1*04:05, HLA-DRB1*07:01, HLA-DRB1*12:01, HLA-DRB1*15:01, HLA-DRB3*01:01, HLA-DPA1*01:03/DPB1*02:01, HLA-DPA1*01:03/HLA-DPB1*04:01, HLA-DPA1*01/DPB1*04:01, HLA-DPA1*02:01/DPB1*01:01, HLA-DPA1*03:01/DPB1*04:02, HLA-DPA1*01:03/HLA-DPB1*04:01, HLA-DPA1*03:01/HLA-DPB1*04:02, HLA-DPA1*02:01/HLA-DPB1*14:01 |
| SEQ ID NO: 103 | FDLFTDVHYSEVSAK | HLA-DRB1*01:01, HLA-DRB1*03:01, HLA-DRB1*07:01, HLA-DRB1*09:01, HLA-DPA1*01:03/DPB1*02:01, HLA-DPA1*01/DPB1*04:01, HLA-DPA1*01:03/HLA-DPB1*04:01, HLA-DPA1*02:01/DPB1*01:01, HLA-DPA1*03:01/DPB1*04:02, HLA-DPA1*02:01/HLA-DPB1*14:01 |
| SEQ ID NO: 104 | GRSENAIVTSRKVQE | HLA-DRB1*01:01, HLA-DRB1*03:01, HLA-DRB1*07:01, HLA-DRB1*11:01, HLA-DRB1*12:01, HLA-DRB5*01:01 |
| SEQ ID NO: 105 | IVTSRKVQEEVFDLF | HLA-DRB1*03:01, HLA-DRB1*11:01, HLA-DPA1*01:03/DPB1*02:01, HLA-DPA1*01/DPB1*04:01, HLA-DPA1*02:01/DPB1*01:01, HLA-DPA1*02:01/DPB1*05:01, HLA-DPA1*02:01/HLA-DPB1*14:01 |
| SEQ ID NO: 106 | KGRSENAIVTSRKVQ | HLA-DRB1*01:01, HLA-DRB1*07:01, HLA-DRB1*11:01, HLA-DRB1*12:01, HLA-DRB5*01:01 |
| SEQ ID NO: 107 | KVQEEVFDLFTDVHY | HLA-DRB1*03:01, HLA-DRB1*04:01, HLA-DRB1*04:05, HLA-DRB1*07:01, HLA-DRB1*15:01, HLA-DPA1*01:03/DPB1*02:01, HLA-DPA1*01/DPB1*04:01, HLA-DPA1*02:01/D?B1*01:01, HLA-DPA1*02:01/DPB1*05:01, HLA-DPA1*03:01/HLA-DPB1*04:02, HLA-DPA1*02:01/HLA-DPB1*14:01 |
| SEQ ID NO: 108 | LFTDVHYSEVSAKTK | HLA-DRB1*01:01, HLA-DRB1*04:01, HLA-DRB1*07:01, HLA-DRB1*09:01, HLA-DRB5*01:01, HLA-DPA1*01:03/DPB1*02:01, |

TABLE 2-continued

LmLRAB

| | | |
|---|---|---|
| SEQ ID NO: 109 | NAIVTSRKVQEEVFD | HLA-DPA1*01/DPB1*04:01, HLA-DPA1*02:01/DPB1*01:01, HLA-DPA1*02:01/HLA-DPB1*14:01 HLA-DRB1*03:01, HLA-DRB1*07:01, HLA-DRB1*08:02, HLA-DRB1*11:01, HLA-DRB1*12:01 |
| SEQ ID NO: 110 | QEEVFDLFTDVHYSE | HLA-DRB1*03:01, HLA-DRB1*04:01, HLA-DRB1*04:05, HLA-DRB1*07:01, HLA-DRB1*15:01, HLA-DRB3*01:01, HLA-DPA1*01:03/DPB1*02:01, HLA-DPA1*01/DPB1*04:01, HLA-DPA1*02:01/DPB1*01:01, HLA-DPA1*03:01/DPB1*04:02, HLA-DPA1*01:03/HLA-DPB1*04:01, HLA-DPA1*02:01/HLA-DPB1*14:01 |
| SEQ ID NO: 111 | RKVQEEVFDLFTDVH | HLA-DRB1*03:01, HLA-DRB1*04:01, HLA-DPA1*01:03/DPB1*02:01, HLA-DPA1*01/DPB1*04:01, HLA-DPA1*02:01/DPB1*01:01, HLA-DPA1*02:01/DPB1*05:01, HLA-DPA1*03:01/DPB1*04:02 |
| SEQ ID NO: 112 | RSENAIVTSRKVQEE | HLA-DRB1*01:01, HLA-DRB1*03:01, HLA-DRB1*07:01, HLA-DRB1*11:01, HLA-DRB5*01:01 |
| SEQ ID NO: 113 | SENAIVTSRKVQEEV | HLA-DRB1*03:01, HLA-DRB1*07:01, HLA-DRB1*08:02, HLA-DRB1*11:01, HLA-DRB1*12:01 |
| SEQ ID NO: 114 | SRKVQEEVFDLFTDV | HLA-DRB1*03:01, HLA-DPA1*01:03/DPB1*02:01, HLA-DPA1*01/DPB1*04:01, HLA-DPA1*02:01/DPB1*01:01, HLA-DPA1*02:01/DPB1*05:01, HLA-DPA1*03:01/DPB1*04:02 |
| SEQ ID NO: 115 | TSRKVQEEVFDLFTD | HLA-DRB1*03:01, HLA-DPA1*01:03/DPB1*02:01, HLA-DPA1*01/DPB1*04:01, HLA-DPA1*02:01/DPB1*01:01, HLA-DPA1*02:01/DPB1*05:01, HLA-DPA1*01:03/HLA-DPB1*04:01, HLA-DPA1*03:01/HLA-DPB1*04:02, HLA-DPA1*02:01/HLA-DPB1*14:01 |
| SEQ ID NO: 116 | VFDLFTDVHYSEVSA | HLA-DRB1*01:01, HLA-DRB1*03:01, HLA-DRB1*04:01, HLA-DRB1*07:01, HLA-DRB1*15:01, HLA-DRB3*01:01, HLA-DPA1*01/DPB1*04:01, HLA-DPA1*01:03/DPB1*02:01, HLA-DPA1*02:01/DPB1*01:01, HLA-DPA1*03:01/DPB1*04:02, HLA-DPA1*01:03/HLA-DPB1*04:01, HLA-DPA1*02:01/HLA-DPB1*14:01 |
| SEQ ID NO: 117 | VQEEVFDLFTDVHYS | HLA-DRB1*03:01, HLA-DRB1*04:01, HLA-DRB1*04:05, HLA-DRB1*07:01, HLA-DRB1*15:01, HLA-DPA1*01:03/DPB1*02:01, HLA-DPA1*01/DPB1*04:01, HLA-DPA1*02:01/DPB1*01:01, HLA-DPA1*02:01/DPB1*05:01, HLA-DPA1*03:01/DPB1*04:02 |
| SEQ ID NO: 118 | VTSRKQEEVFDLFT | HLA-DRB1*03:01, HLA-DPA1*01:03/DPB1*02:01, HLA-DPA1*01/DPB1*04:01, HLA-DPA1*02:01/DPB1*01:01, HLA-DPA1*02:01/DPB1*05:01, HLA-DPA1*01:03/HLA-DPB1*04:01, HLA-DPA1*03:01/HLA-DPB1*04:02, HLA-DPA1*02:01/HLA-DPB1*14:01 |

| | Core | Concatenation affinity for HLA alleles of class II | Affinity for HLA alleles of class I |
|---|---|---|---|
| SEQ ID NO: 119 | AIVTSRKVQ | HLA-DRB1*11:01 | |
| SEQ ID NO: 120 | EVFDLFTDV | HLA-DPA1*01:03/DPB1*02:01, HLA-DPA1*01/DPB1*04:01, HLA-DPA1*03:01/DPB1*04:02, HLA-DPA1*02:01/HLA-DPB1*01:01, HLA-DPA1*01:03/HLA-DPB1*04:01, | HLA-A*02:03, HLA-A*02:06, HLA-A*68:02 |

TABLE 2-continued

LmLRAB

| | | | |
|---|---|---|---|
| | | HLA-DPA1*02:01/ | |
| | | HLA-DPB1*05:01 | |
| SEQ ID NO: 121 | FTDVHYSEV | HLA-DRB1*01:01, | HLA-A*01:01, |
| | | HLA-DRB1*07:01, | HLA-A*02:01, |
| | | HLA-DRB1*09:01, | HLA-A*02:03, |
| | | HLA-DRPA*01:03/ | HLA-A*02:06, |
| | | DPB1*04:01, | HLA-A*35:01, |
| | | HLA-DPA1*01:03/ | HLA-A*68:02 |
| | | DPB1*02:01 | |
| SEQ ID NO: 122 | HYSEVSAKT | HLA-DRB1*04:01 | |
| SEQ ID NO: 123 | IVTSRKVQE | HLA-DRB1*03:01, | |
| | | HLA-DRB1*08:02, | |
| | | HLA-DRB1*11:01 | |
| SEQ ID NO: 124 | LFTDVHYSE | HLA-DRB1*03:01, | |
| | | HLA-DRB3*01:01, | |
| | | HLA-DPA1*01/ | |
| | | DPB1*04:01, | |
| | | HLA-DPA1*02:01/ | |
| | | DPB1*01:01, | |
| | | HLA-DPA1*03:01/ | |
| | | DPB1*04:02 | |
| SEQ ID NO: 125 | NAIVTSRKV | HLA-DRB1*07:01 | |
| SEQ ID NO: 126 | VQEEVFDLF | HLA-DRB1*03:01, | HLA-A*02:06 |
| | | HLA-DPA1*01/ | |
| | | DPB1*04:01, | |
| | | HLA-DPA1*01:03/ | |
| | | DPB1*02:01, | |
| | | HLA-DPA1*02:01/ | |
| | | DPB1*01:01, | |
| | | HLA-DPA1*02:01/ | |
| | | DPB1*05:01, | |
| | | HLA-DPA1*03:01/ | |
| | | DPB1*04:02 | |
| SEQ ID NO: 127 | YSEVSAKTK | HLA-DRB1*07:01, | |
| | | HLA-DRB5*01:01 | |

| | Peptide CII | Concatenation affinity for HLA alleles of class I |
|---|---|---|
| SEQ ID NO: 128 | DVHYSEVSA | HLA-A*68*02 |
| SEQ ID NO: 129 | ENAIVTSRK | HLA-A*68:01 |
| SEQ ID NO: 130 | FDLFTDVHY | HLA-A*02:01, HLA-B*35:01 |
| SEQ ID NO: 131 | KGRSENAIV | HLA-A*30:01 |
| SEQ ID NO: 132 | KVQEEVFDL | HLA-A*02:01, HLA-A*02:06, HLA-A*32:01 |
| SEQ ID NO: 133 | LFTDVHYSEV | HLA-A*01:01 |
| SEQ ID NO: 134 | SENAIVTSR | HLA-A*31:01, HLA-B*44:03, HLA-A*68:01 |
| SEQ ID NO: 135 | TSRKDQEEV | HLA-B*15:01, HLA-A*30:01, HLA-A*68:02 |
| SEQ ID NO: 136 | VHYSEVSAK | HLA-A*03:01 |

Long peptides

| | |
|---|---|
| SEQ ID NO: 137 | SENAIVTSRKVQEEVFDLFTDVHYSEVSAKTK |
| SEQ ID NO: 138 | KGRSENAIVTSRKVQEEVFDLFTDVHYSEVSAKTK |

TABLE 3

PSA

| SEQ ID KC-2.6 | Peptide | Concatenation affinity for HLA alleles of class II |
|---|---|---|
| SEQ ID NO: 139 | EGYFLTDEKTSLVYG | HLA-DRB1*01:01, HLA-DRB1*03:01, |
| | | HLA-DRB1*04:01, HLA-DRB1*04:05, |
| | | HLA-DRB1*07:01, HLA-DRB1*11:01, |
| | | HLA-DRB1*12:01, HLA-DRB1*13:02, |
| | | HLA-DRB3*01:01, HLA-DRB3*02:02, |
| | | HLA-DPA1*02:01/DPB1*01:01, |
| | | HLA-DPA1*03:01/DPB1*04:02 |
| SEQ ID NO: 140 | FLTDEKTSLVYGDGG | HLA-DRB1*03:01, HLA-DRB3*01:01 |
| SEQ ID NO: 141 | GEGYFLTDEKTSLVY | HLA-DRB1*01:01, HLA-DRB1*03:01, |
| | | HLA-DRB1*04:01, HLA-DRB1*04:05, |
| | | HLA-DRB1*07:01, HLA-DRB1*11:01, |
| | | HLA-DRB1*12:01, HLA-DRB1*13:02, |
| | | HLA-DRB3*01:01, HLA-DRB3*02:02, |
| | | HLA-DPA1*02:01/DPB1*01:01, |

TABLE 3-continued

| | PSA | |
|---|---|---|
| SEQ ID NO: 142 | GYFLTDEKTSLVYGD | HLA-DPA1*03:01/DPB1*04:02, HLA-DPA1*02:01/HDPB1*14:01 HLA-DRB1*01:01, HLA-DRB1*03:01, HLA-DRB1*04:01, HLA-DRB1*07:01, HLA-DRB1*11:01, HLA-DRB3*01:01, HLA-DRB3*02:02, HLA-DPA1*02:01/DPB1*01:01, HLA-DPA1*02:01/DPB1*14:01, HLA-DPA1*03:01/DPB1*04:02 |
| SEQ ID NO: 143 | RSGEGYFLTDEKTSL | HLA-DRB1*01:01, HLA-DRB1*03:01, HLA-DRB1*04:01, HLA-DRB3*01:01, HLA-DPA1*03:01/DPB1*14:01 |
| SEQ ID NO: 144 | SGEGYFLTDEKTSLV | HLA-DRB1*01:01, HLA-DRB1*03:01, HLA-DRB1*04:01, HLA-DRB1*04:05, HLA-DRB1*07:01, HLA-DRB1*11:01, HLA-DRB3*01:01, HLA-DRB3*02:02, HLA-DPA1*02:01/DPB1*01:01 |
| SEQ ID NO: 145 | YFLTDEKTSLVYGDG | HLA-DRB1*01:01, HLA-DRB1*03:01, HLA-DRB1*04:01, HLA-DRB3*01:01, HLA-DRB3*02:02, HLA-DPA1*03:01/DPB1*04:02, HLA-DPA1*02:01/DPB1*14:01 |

| | Core | Concatenation affinity for HLA alleles of class II | Affinity HLA alleles of class I |
|---|---|---|---|
| SEQ ID NO: 146 | FLTDEKTSL | HLA-DRB1*01:01, HLA-DRB1*03:01, HLA-DRB1*04:01, HLA-DRB1*11:01, HLA-DRB3*01:01, HLA-DRB3*02:02, HLA-DPA1*02:01/DPB1*01:01, HLA-DPA1*03:01/DPB1*04:02 | HLA-A*02:01, HLA-A*02:03, HLA-A*02:06, HLA-B*39:01 |
| SEQ ID NO: 147 | GYFLTDEKT | HLA-DRB1*04:01, HLA-DPA1*02:01/DPB1*01:01 | |
| SEQ ID NO: 148 | LTDEKTSLV | HLA-DRB1*01:01, HLA-DRB1*04:01 | HLA-A*01:01, HLA-A*02:01, HLA-A*02:03, HLA-A*02:06, HLA-A*68:02 |
| SEQ ID NO: 149 | RSGEGYFLT | HLA-DRB1*03:01, HLA-DRB3*01:01 | |
| SEQ ID NO: 150 | YFLTDEKTS | HLA-DRB1*01:01, HLA-DRB1*04:01, HLA-DRB1*11:01 | |

| | Peptide CII | Concatenation affinity allele CII |
|---|---|---|
| SEQ ID NO: 151 | ARSARSGEGY | HLA-B*15:01 |
| SEQ ID NO: 152 | ARSGEGYFL | HLA-B*39:01 |
| SEQ ID NO: 153 | FLTDEKTSLV | HLA-A*01:01, HLA-A*02:01 |
| SEQ ID NO: 154 | LTDEKTSLVY | HLA-A*01:01, HLA-B*15:01 |
| SEQ ID NO: 155 | RSARSGEGY | HLA-A*30:02, HLA-B*15:01, HLA-B*57:01, HLA-B*58:01 |
| SEQ ID NO: 156 | RSARSGEGYF | HLA-B*15:01, HLA-B*58:01 |

| | Long peptide | |
|---|---|---|
| SEQ ID NO: 157 | KAARSARSGEGYFLTDEKTSLVYGDGG | |

| SEQ ID KC-2.7 | Peptide | Concatenation affinity for HLA alleles of class II |
|---|---|---|
| SEQ ID NO: 158 | DYSHSMIRDLDFSNM | HLA-DRB1*04:01, HLA-DRB1*04:05, HLA-DRB1*07:01, HLA-DRB1*09:01, HLA-DRB1*12:01, HLA-DRB4*01:01, HLA-DPA1*02:01/DPB1*01:01, HLA-DPA1*02:01/DPB1*14:01 |
| SEQ ID NO: 159 | GSDYSHSMIRDLDFS | HLA-DRB1*01:01, HLA-DRB1*04:05, HLA-DRB1*07:01, HLA-DRB1*09:01, HLA-DRB4*01:01, HLA-DRB5*01:01, HLA-DPA1*02:01/DPB1*01:01, HLA-DPA1*02:01/DPB1*14:01 |

TABLE 3-continued

| | | PSA | |
|---|---|---|---|
| SEQ ID NO: 160 | HSMIRDLDFSNMGLL | HLA-DRB1*01:01, HLA-DRB1*03:01, HLA-DRB1*04:01, HLA-DRB1*04:05, HLA-DRB1*07:01, HLA-DRB1*08:02, HLA-DRB1*12:01, HLA-DRB1*13:02, HLA-DRB1*15:01, HLA-DRB4*01:01, HLA-DPA1*01:03-DPB1*02:01, HLA-DPA1*02:01/DPB1*01:01, HLA-DPA1*02:01/DPB1*14:01, HLA-DPA1*03:01/DPB1*04:02 | |
| SEQ ID NO: 161 | IRDLDFSNMGLLLSG | HLA-DRB1*01:01, HLA-DRB1*04:05, HLA-DRB1*07:01, HLA-DRB1*11:01, HLA-DRB1*12:01, HLA-DRB1*13:02, HLA-DRB1*15:01, HLA-DPA1*01:03/DPB1*04:01, HLA-DPA1*01:03/DPB1*02:01, HLA-DPA1*02:01/DPB1*01:01, HLA-DPA1*02:01/DPB1*14:01, HLA-DPA1*03:01/DPB1*04:02 | |
| SEQ ID NO: 162 | MIRDLDFSNMGLLLS | HLA-DRB1*01:01, HLA-DRB1*04:01, HLA-DRB1*04:05, HLA-DRB1*07:01, HLA-DRB1*12:01, HLA-DRB1*13:02, HLA-DRB1*15:01, HLA-DPA1*01:03/DPB1*04:01, HLA-DPA1*01:03/DPB1*02:01, HLA-DPA1*02:01/DPB1*01:01, HLA-DPA1*02:01/DPB1*14:01, HLA-DPA1*03:01/DPB1*04:02 | |
| SEQ ID NO: 163 | MPSGSDYSHSMIRDL | HLA-DRB1*04:05, HLA-DRB1*07:01, HLA-DRB1*09:01, HLA-DRB5*01:01 | |
| SEQ ID NO: 164 | PSGSDYSHSMIRDLD | HLA-DRB1*04:05, HLA-DRB1*07:01, HLA-DRB1*09:01, HLA-DRB5*01:01, LA-DPA1*02:01/DPB1*01:01 | |
| SEQ ID NO: 165 | RDLDFSNMGLLLSGT | HLA-DRB1*01:01, HLA-DRB1*04:05, HLA-DRB1*07:01, HLA-DRB1*11:01, HLA-DRB1*12:01, HLA-DRB1*13:02, HLA-DRB1*15:01, HLA-DPA1*01:03/DPB1*02:01, HLA-DPA1*01:03/DPB1*04:01, HLA-DPA1*02:01/DPB1*01:01, HLA-DPA1*03:01/DPB1*04:02, HLA-DPA1*02:01/DPB1*14:01 | |
| SEQ ID NO: 166 | SDYSHSMIRDLDFSN | HLA-DRB1*01:01, HLA-DRB1*04:01, HLA-DRB1*04:05, HLA-DRB1*07:01, HLA-DRB1*12:01, HLA-DRB1*09:01, HLA-DRB4*01:01, HLA-DPA1*02:01/DPB1*01:01, HLA-DPA1*02:01/DPB1*14:01 | |
| SEQ ID NO: 167 | SGSDYSHSMIRDLDF | HLA-DRB1*01:01, HLA-DRB1*04:05, HLA-DRB1*07:01, HLA-DRB1*09:01, HLA-DRB5*01:01, HLA-DPA1*02:01/DPB1*01:01, HLA-DPA1*02:01/DPB1*14:01 | |
| SEQ ID NO: 168 | SHSMIRDLDGSNMGL | HLA-DRB1*03:01, HLA-DRB1*04:01, HLA-DRB1*04:05, HLA-DRB1*08:02, HLA-DRB1*12:01, HLA-DRB4*01:01 | |
| SEQ ID NO: 169 | SMIRDLDFSNMGLLL | HLA-DRB1*01:01, HLA-DRB1*03:01, HLA-DRB1*04:01, HLA-DRB1*04:05, HLA-DRB1*07:01, HLA-DRB1*08:02, HLA-DRB1*12:01, HLA-DRB1*13:02, HLA-DRB1*15:01, HLA-DRB4*01:01, HLA-DPA1*01:03/DPB1*04:01, HLA-DPA1*01:03/DPB1*02:01, HLA-DPA1*02:01/DPB1*01:01, HLA-DPA1*03:01/DPB1*04:02, HLA-DPA1*02:01/DPB1*14:01 | |
| SEQ ID NO: 170 | YSHSMIRDLDFSNMG | HLA-DRB1*04:01, HLA-DRB1*04:05, HLA-DRB1*07:01, HLA-DRB1*08:02, HLA-DRB1*09:01, HLA-DRB1*12:01, HLA-DRB4*01:01 | |

| | Core | Concatenation affinity for HLA alleles of class II | Affinity for HLA alleles of class I |
|---|---|---|---|
| SEQ ID NO: 171 | DFSNMGLLL | HLA-DPA1*01:03/DPB1*04:01, HLA-DPA1*03:01/DPB1*04:02 | |

TABLE 3-continued

| | | PSA | |
|---|---|---|---|
| SEQ ID NO: 172 | FSNMGLLLS | HLA-DRB1*01:01, HLA-DRB1*11:01 | |
| SEQ ID NO: 173 | HSMIRDLDF | HLA-DRB4*01:01 | HLA-B*35:01, HLA-B*58:01 |
| SEQ ID NO: 174 | IRDLDFSNM | HLA-DRB1*01:01, HLA-DRB4*01:01 | |
| SEQ ID NO: 175 | LDFSNMGLL | HLA-DRB1*07:01, HLA-DRB1*13:02, HLA-DRB1*15:01, HLA-DPA1*02:01/DRPB*01:01, HLA-DPA1*01:03/DPB1*02:01, HLA-DPA1*02:01/DPB1*01:01, HLA-DPA1*03:01/DPB1*04:02 | |
| SEQ ID NO: 176 | MIRDLDFSN | HLA-DRB1*03:01, HLA-DRB1*04:01, HLA-DRB1*04:05, HLA-DRB1*08:02 | |
| SEQ ID NO: 177 | SDYSHSMIR | HLA-DRB1*07:01, HLA-DRB5*01:01 | HLA-A*31:01, HLA-A*68:01 |
| SEQ ID NO: 178 | YSHSMIRDL | HLA-DRB1*01:01, HLA-DRB1*04:05, HLA-DRB1*07:01, HLA-DRB1*09:01, HLA-DPA1*02:01/DPB1*01:01 | |

| | Peptide | Concatenation affinity for HLA alleles of class I |
|---|---|---|
| SEQ ID NO: 179 | GSDYSHSMIR | HLA-A*03:01 |
| SEQ ID NO: 180 | KEMPSGSDY | HLA-B*15:01, HLA-A*30:02, HLA-B*44:02, HLA-B*44:03 |
| SEQ ID NO: 181 | MIRDLDFSNM | HLA-B*15:01 |
| SEQ ID NO: 182 | MPSGSDYSH | HLA-B*35:01, HLA-B*53:01 |
| SEQ ID NO: 183 | NMGLLLSGT | HLA-A*02:02 |
| SEQ ID NO: 184 | SMIRDLDFS | HLA-A*02:03, HLA-A*02:06 |

| | Long peptide | |
|---|---|---|
| SEQ ID NO: 185 | KEMPSGSDYSHMSIRDLDFSNMGLLLSGT | |

More preferentially, the sequences of these epitopes contained in the peptide compounds according to the invention are chosen from the sequences SEQ ID NO: 1 to 21, the sequences SEQ ID NO: 24 to 64, the sequences SEQ ID NO: 67, 68, 70 to 72, 74 to 76, the sequences SEQ ID NO: 78 to 95, the sequences SEQ ID NO: 98 to 136, the sequences SEQ ID NO: 139 to 156, and the sequences SEQ ID NO: 158 to 184, listed in Tables 1, 2 and 3 above, as well as the analogous, mutein and homologous derivatives thereof.

The object of the invention is a peptidic compound consisting of epitopes as described above and comprising:
1 to 21 overlapping epitopes of sequences SEQ ID NO: 1 to 21 such as the sequences SEQ ID NO: 22 and 23, or
1 to 41 overlapping epitopes of sequences SEQ ID NO: 24 to 64 such as the sequences SEQ ID NO: 65 and 66, or
(iii) 1 to 18 overlapping epitopes of sequences SEQ ID NO: 78 to 95 such as the sequences SEQ ID NO: 96 and 97, or
(iv) 1 to 39 overlapping epitopes of sequences SEQ ID NO: 98 to 136 such as the sequences SEQ ID NO: 137 and 138, or
(v) 1 to 18 overlapping epitopes of sequences SEQ ID NO: 139 to 156, such as the sequence SEQ ID NO: 157, or
(vi) 1 to 27 overlapping epitopes of sequences SEQ ID NO: 158 to 184 such as the sequence SEQ ID NO: 185, or (viii) 1 to 3 epitopes of sequences SEQ ID NO: 67, 68, 70 to 72, 74 to 76 such as the sequences SEQ ID NO: 69, 73 and 77, optionally separated by a peptide spacer or a linking peptide sequence comprising 1 to 8 amino acids.

By way of non-limitative example of a peptidic spacer or linking sequence, mention can be made of the ARY, KGR, RY, GR, TV, K, V, Y and L units among others (Stittelaar K, et al. Vaccine, 2002, 20: 249-261; Lee Y. et al., Biomed Microdevices, 2010, 12: 207-222; Cardinaud, S., et al. Aids, 2009, 23: 1945-1954). Preferably, the peptide spacers or linking sequences used are K, KGR, RY, ARY or KARY and analogs thereof.

More preferentially, the multiepitopic peptide compounds according to the invention are chosen from the nine sequences SEQ ID NO: 23, 66, 69, 73, 77, 97, 138, 157 and 185, as well as the analogous, mutein and homologous derivatives thereof. These nine multiepitopic peptide compounds of SEQ ID NO: 23, 66, 69, 73, 77, 97, 138, 157 and 185 are for example synthesis multiepitopic peptide compounds, associated or not with peptides of the prior art having affine epitopes for the HLA molecules of class I.

The multiepitopic peptide compounds (24 to 40-mer), having a high affinity with a maximized number of HLA molecules of class I and of class II, such as the affinities for the alleles HLA of class I and HLA of class II of the epitopes in the peptides of the sequences SEQ ID NO: 22, 23, 65, 66, 69, 73, 77, 96, 97, 137, 138, and 157, 185, have a high immunoprevalent potential corresponding to an optimal vaccine coverage, in particular for the populations concerned. The degree of coverage of the peptide compounds of the invention show a very high added value compared with the peptides of the prior art. The coverage of the estimated world population with a combination of the peptide compounds according to the invention, or with the combination of the peptides B9, B10, B11, B12 and B13 (SEQ ID NO: 186 to 190), shows a very high added value of the peptides according to the invention.

The in vitro efficacy of the peptide compounds for stimulating human cells and producing cytokines of type Th1 such as IFN-γ has been evaluated, in combinations at 1 μM for each peptide, using blood samples from individuals cured of leishmaniasis, according to a short protocol and a single stimulation. As is shown in the table in FIG. 4, the IFN-γ levels secreted by the stimulated T cells can attain more than 2590 pg/ml with a combination of the peptide compounds proposed and associated with peptides of the prior art, and more than 2700 pg/ml with a combination of the proposed peptide compounds not associated with these peptides. These levels show a very high added value compared with the peptides of the prior art corresponding to "Pool Z" in the table in FIG. 4. In this table, "Cured CL 1 to 6" are individuals cured of cutaneous leishmaniasis, "Naive 1 to 6" are naive individuals (non-immune control), "NS" corresponds to "not stimulated" (environment alone) after 5 days ("NS 5 days") and 10 days ("NS 10 days") of culture, "PHA" is phytohemagglutinin (positive stimulation control), "SLA" corresponds to the total soluble antigens of Leishmania major, and "Pool A to G" correspond to combinations of the synthesis peptide compounds of sequence SEQ ID NO: 23, 66, 69, 73, 77, 97, 138, 157 and 185, associated (Pool A, B, C, D, F) or not (Pool E, G) with synthesis peptide compounds of the prior art. The values of IFN-γ for "PHA" and "SLA" are the values subtracted from the "NS 5 days" values, the values of IFN-γ for the "Pool A to Z" are the values subtracted from the values of "NS 10 days" and the values in bold correspond to values higher than the mean of the naive+3×standard deviation. The in vitro immunogenicity of the peptide compounds is the ability of the peptides to recruit precursive lymphocytes, to induce in vitro a stimulation of specific T lymphocytes with the production of IFN-γ.

The immunogenicity was evaluated, with combinations of peptides (combination corresponding to the "Pool H") at 1 μM for each peptide, from samplings of blood of naive individuals and according to a long protocol with at least three successive stimulations. An IFN-γ ELISPOT test for measuring the frequency of the pre-existing naive T cells and the amplitude of the specific naive T repertoire for each peptide, was performed with the CD4+ T cells and the autologous dendritic cells of a naive individual in the presence or absence of the mixture of peptides, or in the presence of each peptide individually. Several specific lines of the peptide combination were revealed and respond specifically to at least one of the peptides of the present invention. The "Pool H" combination was used either with peptides not modified at the amino-terminal end and with amidation of the carboxy-terminal end, or with peptides chemically modified by a palmitoyl tail at the amino-terminal end and with amidation of the carboxy-terminal end.

The evaluation of the immunogenicity properties of peptide compounds according to the invention in naive individuals, persons who have never been in contact with the Leishmania parasite, is an important factor in predicting the efficacy of a peptide vaccine (Kwok WW et al, 2012, Frequency of epitope-specific naive CD4(+) T cells correlates with immunodominance in the human memory repertoire; Castelli F A et al, 2007, Differential capacity of T cell priming in naive donors of promiscuous CD4+ T cell epitopes of HCV NS3 and Core proteins). Immunogenicity is evaluated in vitro by measuring the frequency of the pre-existing naive T cells and the amplitude of the naive T repertoire specific for each compound. The evaluation is carried out using blood samples from naive individuals and in accordance with a long protocol (Castelli F A, et al. 2007 as aforementioned) putting purified T lymphocytes in contact with autologous dendritic cells previously incubated with the peptides of the invention. The combination of peptides used is composed of: SEQ ID NO: 23, SEQ ID NO: 66, SEQ ID NO: 73, SEQ ID NO: 77, SEQ ID NO: 97, SEQ ID NO: 138, SEQ ID NO: 157, SEQ ID NO: 185, SEQ ID NO: B11, SEQ ID NO: B12 and SEQ ID NO: B13. The compounds were synthesized chemically without amino-terminal modification and with carboxy-terminal (peptide-NH2) amidation (NH2). After three successive stimulations at intervals of seven days of the CD4+ T cells of a naive individual (MPL10; Établissement français du sang de Toulouse), an IFN-γ ELISPOT was carried out with the cells in the presence or absence of the mixture of peptides, or in the presence of each compound individually. Six specific lines were revealed (p-value between 0.0269 and 0.0489 according to the specific line). Each positive line responds to at least one of the peptides of the present invention. The MPL10-3 line responds to the peptides SEQ ID NO: 73 and SEQ ID NO: 157. The MPL10-4 line responds to the peptides SEQ ID NO: 23, SEQ ID NO: 73, SEQ ID NO: 77, SEQ ID NO: 97, SEQ ID NO: 138 and SEQ ID NO: 157. The MPL10-7 line responds to the peptides SEQ ID NO: 77, SEQ ID NO: 97 and SEQ ID NO: 157. The MPL10-8 line responds to the peptides SEQ ID NO: 66, SEQ ID NO: 73, SEQ ID NO: 97, SEQ ID NO: 138 and SEQ ID NO: 157. The MPL10-10 line responds to the peptides SEQ ID NO: 66, SEQ ID NO: 73, SEQ ID NO: 77, SEQ ID NO: 97, SEQ ID NO: 138, SEQ ID NO: 157 and SEQ ID NO: 185. And the MPL10-12 line responds to the peptides SEQ ID NO: 66, SEQ ID NO: 157 and SEQ ID NO: 185.

The evaluation of the immunogenicity properties of peptide compounds of the invention in the same naive individual (MPL10) but with chemically synthesized compounds with the addition of a palmitoylated tail at the amino-terminal end and with an NH2 group at the carboxy-terminal end (PAL-peptide-NH2) was also performed. The same combination of peptides as before was used. After three stimulations with the mixture of PAL-peptide-NH2 peptides, an IFN-g ELISPOT was carried out with the cells in the presence or absence of the mixture of peptides, or in the presence of each peptide individually. Four specific lines were revealed (p-value=0.0275 for all the specific lines). The MPL10-PAL-2 line responds to the peptides SEQ ID NO: 22, SEQ ID NO: 66, SEQ ID NO: 73, SEQ ID NO: 157 and SEQ ID NO: 185. The MPL10-PAL-3 line responds to the peptides SEQ ID NO: 23, SEQ ID NO: 66, SEQ ID NO: 73, SEQ ID NO: 77, SEQ ID NO: 97, SEQ ID NO: 138, SEQ ID NO: 157 and SEQ ID NO: 185.

The invention further relates to a composition as a pharmaceutical product, for human or veterinary use, comprising at least:
    an epitope of a sequence chosen from among the sequences SEQ ID No: 1 to 21, the sequences SEQ ID NO: 24 to 64, the sequences SEQ ID NO: 67, 68, 70 to 72, 74 to 76, the sequences SEQ ID NO: 78 to 95, the sequences SEQ ID NO: 98 to 136, the sequences SEQ ID NO: 139 to 156, and the sequences SEQ ID NO: 158 to 184, or a peptidic compound comprising 1, 2, 3 or 4 of the epitopes of sequence SEQ ID NO: 1 to 21, SEQ ID NO: 24 to 64, SEQ ID NO: 67, 68, 70 to 72, 74 to 76, SEQ ID NO: 78 to 95, SEQ ID NO: 98 to 136, SEQ ID NO: 139 to 156, and SEQ ID NO: 158 to 184, optionally separated by a spacer as defined above, or a peptidic compound of sequence chosen from SEQ ID NO: 22, 23, 65, 66, 69, 73, 77, 96, 97, 137, 138, 157 and 185.

The invention also relates to such a composition for use thereof in prophylactic and therapeutic vaccination directed against one or more of the *Leishmania* such as *Leishmania donovani, Leishmania infantum, Leishmania chagasi, Leishmania mexicana, Leishmania amazonensis, Leishmania venezuelensis, Leishmania tropica, Leishmania major, Leishmania aethiopica, Leishmania (Viannia) braziliensis, Leishmania (Viannia) guyanensis, Leishmania(Viannia) panamensis, Leishmania (Viannia) peruviana.*

Advantageously, the composition according to the invention is able to be used in prophylactic and therapeutic vaccination directed against at least three, preferably at least seven, preferably again at least ten and even more preferably against all the *Leishmania* listed above.

The composition advantageously comprises an adjuvant chosen from the adjuvants chosen from among the Toll-Like Receptor adjuvants of classes TLR3, TLR4, TLR5, TLR7, TLR8, TLR9, saponins and the QA21, quilA or QS21 derivatives thereof, oil in water or water in oil emulsions, polysaccharides, cationic liposomes, virosomes or polyelectrolytes and immunomodulators chosen from sandfly saliva proteins, cytokines, peptides and heat shock proteins, for example HSP70.

Preferably, the composition according to the invention is administered subcutaneously, intradermally, by intramuscular route, intravenously, parenterally, endonasally, or by mucosal or oral route, and is therefore in a form suitable for such administrations.

An additional object of the invention relates to a composition as defined above by way of drug, vaccine or in vitro and/or in vivo diagnostic reagent, for inducing or diagnosing, in a mammal, change from a type Th2 immune state to a type Th1 immune state.

A further additional object of the invention relates to a vaccine capable of conferring cross immunoprotection vis-àvis kinds of leishmaniasis. The significant antigen community shared by *Leishmania* makes it possible to envisage the development of a multipurpose single vaccine, consisting of highly preserved common immunogens. Targeting as a vaccine one or more antigens common to all the species of *Leishmania* would without any doubt represent a real advantage in terms of cross vaccination. Such a vaccine comprises at least:

an epitope of sequence chosen from among the sequences SEQ ID NO: 1 to 21, the sequences SEQ ID NO: 24 to 64, the sequences SEQ ID NO: 67, 68, 70 to 72, 74 to 76, the sequences SEQ ID NO: 78 to 95, the sequences SEQ ID NO: 98 to 136, the sequences SEQ ID NO: 139 to 156, and the sequences SEQ ID NO: 158 to 184, or a peptidic compound comprising 1, 2, 3 or 4 of the epitopes of sequence SEQ ID NO: 1 to 21, SEQ ID NO: 24 to 64, SEQ ID NO: 67, 68, 70 to 72, 74 to 76, SEQ ID NO: 78 to 95, SEQ ID NO: 98 to 136, SEQ ID NO: 139 to 156, and SEQ ID NO: 158 to 184, optionally separated by a spacer as defined above, or a peptidic compound of sequence chosen from SEQ ID NO: 22, 23, 65, 66, 69, 73, 77, 96, 97, 137, 138, 157 and 185.

Such a vaccine is advantageously used for prophylactic or therapeutic vaccination directed against one or more of the *Leishmania* chosen from *Leishmania donovani, Leishmania infantum, Leishmania chagasi, Leishmania mexicana, Leishmania amazonensis, Leishmania venezuelensis, Leishmania tropica, Leishmania major, Leishmania aethiopica, Leishmania (Viannia) braziliensis, Leishmania (Viannia) guyanensis, Leishmania (Viannia) panamensis* and *Leishmania (Viannia) peruviana.*

The vaccine that is the object of the invention is advantageously intended for humans, canines, felines and members of the horse family. Preferentially, the vaccine that is the object of the invention is intended for humans and dogs.

The invention claimed is:

1. Peptidic compound comprising at least two epitopes contained in at least two protein sequences chosen from the *Leishmania* PSA, H2B or LmLRAB proteins, the at least two protein sequences including a protein sequence and a second protein sequence, each of the first protein sequence and the second protein sequence being chosen from the group consisting of
   (1) a first sub-group of protein sequences from the *Leishmania* H2B consisting of:
   sequences SEQ ID NO: 1 to 21,
   sequences SEQ ID NO: 24 to 64,
   (2) a second sub-group protein sequences from the *Leishmania* LmRAB consisting of:
   sequences SEQ ID NO: 67, 68, 70 to 72, 74 to 76,
   sequences SEQ ID NO: 78 to 95,
   sequences SEQ ID NO: 98 to 136,
   sequences SEQ ID NO: 139 to 156,
   (3) a third sub-group of protein sequences from the *Leishmania* PSA consisting of:
   sequences SEQ ID NO: 158 to 184,
   wherein the first protein sequence and the second protein sequence are chosen from different sub-groups among the first, second, and third sub-groups,
   the first and second protein sequences optionally being separated by a peptide spacer comprising at least one amino acid,
   wherein the peptidic compound has immunogenic capability against *Leishmania*.

2. Peptidic compound according to claim 1, wherein the first and second protein sequences are separated by a peptide spacer and the peptidic spacer comprises 1 to 8 amino acids.

3. Peptidic compound according to claim 1, which comprises at least three of the protein sequences.

4. Peptidic compound according to claim 3, wherein the at least three protein sequences include a third protein sequence chosen from the group consisting of
   (1) a first sub-group of protein sequences from the *Leishmania* H2B consisting of:
   sequences SEQ ID NO: 1 to 21,
   sequences SEQ ID NO: 24 to 64,
   (2) a second sub-group of protein sequences from *Leishmania* LmRAB consisting of:
   sequences SEQ ID NO: 67, 68, 70, to 72, 74 to 76,
   sequences SEQ ID NO: 78 to 95,
   sequences SEQ ID NO: 98 to 136,
   sequences SEQ ID NO: 139 to 156,
   (3) a third sub-group of protein sequences from the *Leishmania* PSA consisting of:
   sequences SEQ ID NO: 158 to 184,
   wherein the first protein sequence, the second protein sequences, and the third protein sequences are chosen from different sub-groups among the first, second, and third sub-groups.

5. Peptidic compound according to claim 1, which is linked to a carrier group that increases the immunogenic capability of the peptidic compound against *Leishmania*, as compared to an identical peptidic compound not linked to the carrier group.

6. Peptidic compound according to claim 1, wherein the first protein sequence is SEQ ID NO: 185 and the second protein sequence is chosen from the group consisting of SEQ ID NO: 22, 23, 65, 66, 69, 73, 77, 96, 97, 137, 138, and 157.

7. Peptidic compound according to claim 1, which comprises 2, 3, or 4 of the protein sequences.

8. Pharmaceutical composition comprising at least one peptidic compound according to claim 1.

9. Composition comprising at least one peptidic compound according to claim 1, wherein the composition is formulated for use in prophylactic and therapeutic vaccination directed against *Leishmania*.

10. Composition for use thereof according to claim 9, wherein the *Leishmania* is selected from the group consisting of *Leishmania donovani*, *Leishmania infantum*, *Leishmania chagasi*, *Leishmania mexicana*, *Leishmania amazonensis*, *Leishmania venezuelensis*, *Leishmania tropica*, *Leishmania major*, *Leishmania aethiopica*, *Leishmania (Viannia) braziliensis*, *Leishmania (Viannia) guyanensis*, *Leishmania (Viannia) panamensis*, *Leishmania (Viannia) peruviana*, and combinations of two or more thereof.

11. Composition comprising at least one peptidic compound according to claim 1, wherein the composition is formulated for manufacturing a drug or a vaccine an in vivo or in vitro diagnostic reagent for inducing or diagnosing in mammals an activation of type Th1 lymphocyte-dependent cell-mediated immunity and/or effector humoral immunity.

12. Prophylactic and/or therapeutic vaccine for use thereof against one or more of the *Leishmania* chosen from *Leishmania donovani*, *Leishmania infantum*, *Leishmania chagasi*, *Leishmania mexicana*, *Leishmania amazonensis*, *Leishmania venezuelensis*, *Leishmania tropica*, *Leishmania major*, *Leishmania aethiopica*, *Leishmania braziliensis*, *Leishmania (Viannia) guyanensis*, *Leishmania (Viannia) panamensis*, and/or *Leishmania (Viannia) peruviana*, comprising at least one peptidic compound according to claim 1.

13. Vaccine according to claim 12, which comprises at least one peptidic compound chosen from the group consisting of SEQ ID NO: 22, 23, 69, 73, 77, 65, 66, 96, 97, 137, 138, 157, and 185.

14. Vaccine according to claim 12, which comprises, firstly, at least one peptidic compound chosen from the group consisting of SEQ ID NO: 22, 23, 69, 73, and 77; and secondly, at least one peptidic compound chosen from the group consisting of sequences SEQ ID NO: 65, 66, 96, 97, 137, 138, 157, and 185.

15. Vaccine according to claim 12, which comprises, in combination, the following multiepitopic peptidic compounds:
   each of SEQ ID NO: 66, 157 and 185.

16. Vaccine according to claim 12, which further comprises an adjuvant chosen from the group consisting of
   adjuvants in classes TLR3, TLR4, TLR5, TLR7, TLR8, TLR9, saponins,
   QA21, quilA and QS21 derivatives thereof,
   oil in water emulsions,
   water in oil emulsions,
   polysaccharides,
   cationic liposomes, virosomes, polyelectrolytes, and immunomodulators chosen from the group consisting of sandfly saliva proteins, cytokines, peptides and heat shock proteins.

17. Vaccine according to claim 12, which is formulated for at least one manner of administration selected from the group consisting of subcutaneous, intradermal, intramuscular, parenteral, endonasal, mucosal and oral administration.

18. Diagnostic reagent comprising a peptidic compound according to claim 1.

19. Peptidic compound according to claim 5, wherein the carrier group is selected from the group consisting of keyhole limpet hemocyanin carrier proteins and lipopeptides modified by isoprenylation, N-myristoylation, palmitoylation, 10 S-acylation, or glypiation.

20. Vaccine according to claim 15, which comprises, in combination, the following multiepitopic peptidic compounds:

each of SEQ ID NO: 23, 66, 73, 77, 97, 138, 157 and 185.

21. Vaccine according to claim 15, which comprises, in combination, the following multiepitopic peptidic compounds:

each of SEQ ID NO: 23, 66, 157 and 185.

22. Vaccine according to claim 15, which comprises, in combination, the following multiepitopic peptidic compounds:

each of SEQ ID NO: 66, 97, 138, 157 and 185.

* * * * *